United States Patent
Moskowitz et al.

(10) Patent No.: US 11,135,072 B2
(45) Date of Patent: Oct. 5, 2021

(54) ARTIFICIAL DISC SYSTEM

(71) Applicant: Moskowitz Family LLC, Rockville, MD (US)

(72) Inventors: Nathan C. Moskowitz, Rockville, MD (US); Mosheh T. Moskowitz, Rockville, MD (US); Daniel Glozman, Kefar Adummim (IL)

(73) Assignee: Moskowitz Family LLC, Rockville, MD (US)

( * ) Notice: Subject to any disclaimer, the term of this patent is extended or adjusted under 35 U.S.C. 154(b) by 268 days.

(21) Appl. No.: 16/194,976

(22) Filed: Nov. 19, 2018

(65) Prior Publication Data

US 2019/0105181 A1    Apr. 11, 2019

Related U.S. Application Data

(60) Continuation of application No. 12/889,328, filed on Sep. 23, 2010, now Pat. No. 10,130,493, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/442* (2013.01); *A61F 2002/305* (2013.01);
(Continued)

(58) Field of Classification Search
CPC ...... A61F 2002/4625; A61F 2002/4627; A61F 2/4611; A61F 2230/0015;
(Continued)

(56) References Cited

U.S. PATENT DOCUMENTS 200,238 A    2/1878  Alker
1,553,623 A  9/1925  McLeod
(Continued)

FOREIGN PATENT DOCUMENTS

WO    WO 2004/041129    5/2004

OTHER PUBLICATIONS

Vincent C. Traynelis, "Prosthetics and Biologics: The Wave of the Future" Clinical Neurosurgery, vol. 50, Proceedings of the Congress of Neurological Surgeons, Philadelphia, PA 2002, Chapter 9, pp. 207-219.
(Continued)

*Primary Examiner* — Jessica Weiss
(74) *Attorney, Agent, or Firm* — Fish & Richardson P.C.

(57) ABSTRACT

A total artificial expansile disc and a method for posterior insertion between a pair of vertebral endplates are disclosed. The total artificial expansile disc includes at least one pair of substantially parallel plates that move apart along a first axis, in order to occupy a space defined by the vertebral endplates. In another embodiment, each of substantially parallel plates includes a first plate and a second sliding plate. An expansion device or tool is used to move the substantially parallel pair of plates apart along the first axis. A core is disposed between the pair of plates, and the core permits the vertebral endplates to move relative to one another. A ball limiter or ball extender prevents the core from being extruded from between the substantially parallel plates.

22 Claims, 24 Drawing Sheets

Related U.S. Application Data division of application No. 11/487,415, filed on Jul. 17, 2006, now Pat. No. 7,854,766.

(60) Provisional application No. 60/788,720, filed on Apr. 4, 2006.

(52) U.S. Cl.
CPC .............. A61F 2002/3055 (2013.01); A61F 2002/30133 (2013.01); A61F 2002/30242 (2013.01); A61F 2002/30525 (2013.01); A61F 2002/30538 (2013.01); A61F 2002/30556 (2013.01); A61F 2002/30579 (2013.01); A61F 2002/30663 (2013.01); A61F 2002/30841 (2013.01); A61F 2002/4622 (2013.01); A61F 2002/4627 (2013.01); A61F 2002/4628 (2013.01); A61F 2220/0025 (2013.01); A61F 2230/0015 (2013.01); A61F 2230/0071 (2013.01); A61F 2250/0006 (2013.01); A61F 2250/0009 (2013.01); A61F 2310/00023 (2013.01); A61F 2310/00029 (2013.01)

(58) Field of Classification Search
CPC ...... A61F 2230/0071; A61F 2250/0006; A61F 2250/0009; A61F 2310/00023; A61F 2310/00029; A61F 2220/0025
USPC .................. 606/99–100; 623/17.11–17.16
See application file for complete search history.

(56) References Cited

U.S. PATENT DOCUMENTS

| | | | |
|---|---|---|---|
| 2,090,872 A | 8/1937 | Lamb | |
| 2,214,985 A | 9/1940 | Bachmann | |
| 4,554,914 A | 11/1985 | Kapp et al. | |
| 4,636,217 A | 1/1987 | Ogilvie et al. | |
| 4,759,766 A | 7/1988 | Buettner-Janz et al. | |
| 4,960,420 A | 10/1990 | Goble et al. | |
| 4,997,432 A | 3/1991 | Keller | |
| 5,123,926 A | 6/1992 | Pisharodi | |
| 5,401,269 A | 3/1995 | Buettner-Janz et al. | |
| 5,514,180 A | 5/1996 | Heggeness et al. | |
| 5,660,188 A | 8/1997 | Groiso | |
| 5,667,472 A | 9/1997 | Finn et al. | |
| 5,782,832 A | 7/1998 | Larsen et al. | |
| 5,951,564 A | 9/1999 | Schroder et al. | |
| 5,960,522 A | 10/1999 | Boe | |
| 5,984,922 A | 11/1999 | McKay | |
| 6,113,637 A | 9/2000 | Gill et al. | |
| 6,126,689 A | 10/2000 | Brett | |
| 6,174,311 B1 | 1/2001 | Branch et al. | |
| 6,193,757 B1 | 2/2001 | Foley et al. | |
| 6,261,296 B1 | 7/2001 | Aebi et al. | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,436,101 B1 | 8/2002 | Hamada | |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,540,785 B1 | 4/2003 | Gill et al. | |
| 6,572,653 B1 | 6/2003 | Simonson | |
| 6,579,318 B2 | 6/2003 | Varga et al. | |
| 6,582,468 B1 | 6/2003 | Gauchet | |
| 6,610,093 B1 | 8/2003 | Pisharodi | |
| 6,641,614 B1 | 11/2003 | Wagner et al. | |
| 6,719,794 B2 | 4/2004 | Gelber | |
| 6,723,126 B1 | 4/2004 | Berry | |
| 6,730,088 B2 | 5/2004 | Yeh | |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,866,682 B1 | 3/2005 | An et al. | |
| 6,899,735 B2 | 5/2005 | Coates et al. | |
| 6,904,308 B2 | 6/2005 | Frisch et al. | |
| 6,908,484 B2 | 6/2005 | Zubok et al. | |
| 6,955,671 B2 | 10/2005 | Uchikubo | |
| 6,981,989 B1 | 1/2006 | Fleischmann et al. | |
| 7,018,415 B1 | 3/2006 | McKay | |
| 7,030,904 B2 | 4/2006 | Adair et al. | |
| 7,037,258 B2 | 5/2006 | Chatenever et al. | |
| 7,097,615 B2 | 8/2006 | Banik et al. | |
| 7,115,144 B2 | 10/2006 | Diaz et al. | |
| 7,118,580 B1 | 10/2006 | Beyersdorff et al. | |
| 7,217,293 B2 | 5/2007 | Branch | |
| 7,250,060 B2 | 7/2007 | Trieu | |
| 7,927,373 B2 * | 4/2011 | Parsons ................. A61F 2/4611 623/17.14 |
| 2002/0045904 A1 | 4/2002 | Fuss et al. | |
| 2003/0229355 A1 | 12/2003 | Keller | |
| 2004/0088054 A1 | 5/2004 | Berry | |
| 2004/0088064 A1 | 5/2004 | Berry | |
| 2004/0177531 A1 | 9/2004 | DiBenedetto et al. | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0085910 A1 | 4/2005 | Sweeney | |
| 2005/0216084 A1 | 9/2005 | Fleischmann et al. | |
| 2005/0273170 A1 | 12/2005 | Navarro et al. | |
| 2005/0273174 A1 | 12/2005 | Gordon et al. | |
| 2005/0278026 A1 | 12/2005 | Gordon et al. | |
| 2006/0025777 A1 * | 2/2006 | Weber ................... A61F 2/4611 606/99 |
| 2006/0036325 A1 | 2/2006 | Paul et al. | |
| 2006/0136062 A1 * | 6/2006 | DiNello ................ A61F 2/4425 623/17.14 |
| 2006/0155377 A1 | 7/2006 | Beaurain et al. | |
| 2006/0178745 A1 | 8/2006 | Bartish et al. | |
| 2006/0195192 A1 | 8/2006 | Gordon et al. | |
| 2006/0276902 A1 * | 12/2006 | Zipnick ............... A61B 17/1671 623/17.16 |
| 2007/0010826 A1 | 1/2007 | Rhoda et al. | |
| 2007/0055378 A1 | 3/2007 | Ankney et al. | |
| 2007/0072475 A1 * | 3/2007 | Justin .................... A61F 2/4425 439/354 |
| 2007/0073311 A1 | 3/2007 | Williams | |
| 2007/0073400 A1 | 3/2007 | Paul | |
| 2007/0093901 A1 | 4/2007 | Grotz et al. | |
| 2007/0100347 A1 | 5/2007 | Stad | |
| 2007/0100455 A1 | 5/2007 | Parsons | |
| 2007/0123903 A1 | 5/2007 | Raymond et al. | |
| 2007/0123904 A1 | 5/2007 | Stad et al. | |
| 2007/0198089 A1 | 8/2007 | Moskowitz et al. | |
| 2007/0233254 A1 | 10/2007 | Grotz et al. | |
| 2008/0014719 A1 | 1/2008 | Shibata | |
| 2008/0015698 A1 * | 1/2008 | Marino ................. A61F 2/4425 623/17.15 |
| 2009/0018661 A1 * | 1/2009 | Kim ...................... A61F 2/4611 623/17.16 |
| 2009/0204219 A1 | 8/2009 | Beaurain et al. | |
| 2010/0249797 A1 | 9/2010 | Trudeau | |
| 2010/0286784 A1 * | 11/2010 | Curran ................. A61F 2/4611 623/17.16 |

OTHER PUBLICATIONS

E.K. Wai et al., Disk Re!,P.lacement Arthroplaslies: Can the Success of Hip and Knee Replacements be Repeated in the Spine?, Seminars in Spine Surgery, vol. 15, No. 4 (Dec. 2003), pp. 473-482.

Richard D. Guyer et al., "intervertebral Disc Prostheses," Spine Journal, vol. 28, No. 15S, Supp. to 811103, pp. S15-S23.

International Search Report (ISR) and Written Opinion of the International Searching Authority, dated Dec. 3, 2007, International Application No. PCT/US 07/05005.

Dieter Grob et al., "Clinical Ex~perience With the Dynesys Semi-rigid Fixation System for the Lumbar Spine," Spine, vol. 30, No. 3, 2005, pp. 24-331.

* cited by examiner

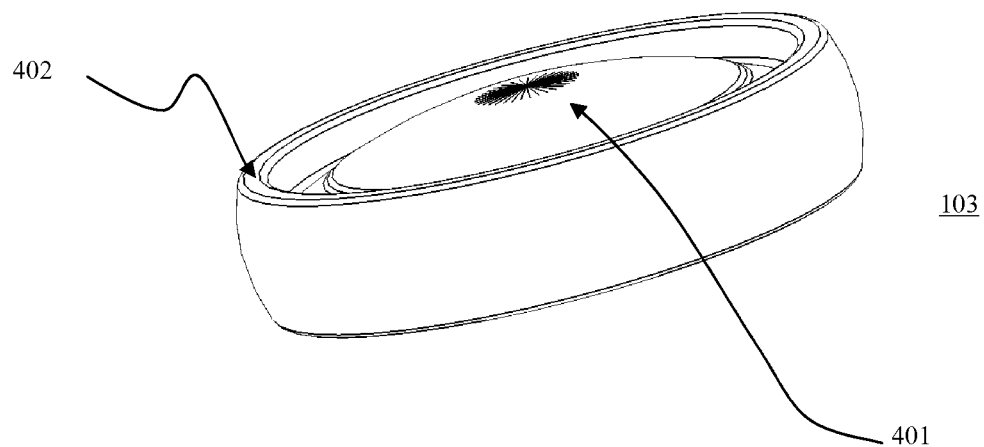
Fig. 4A(1)
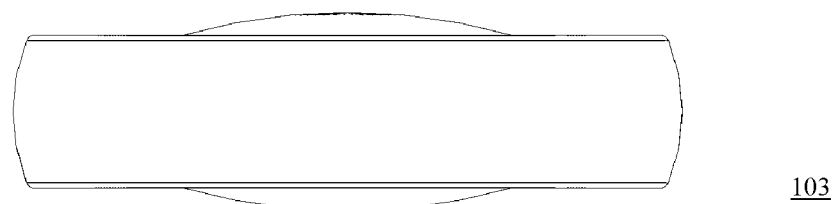
Fig. 4A(2)

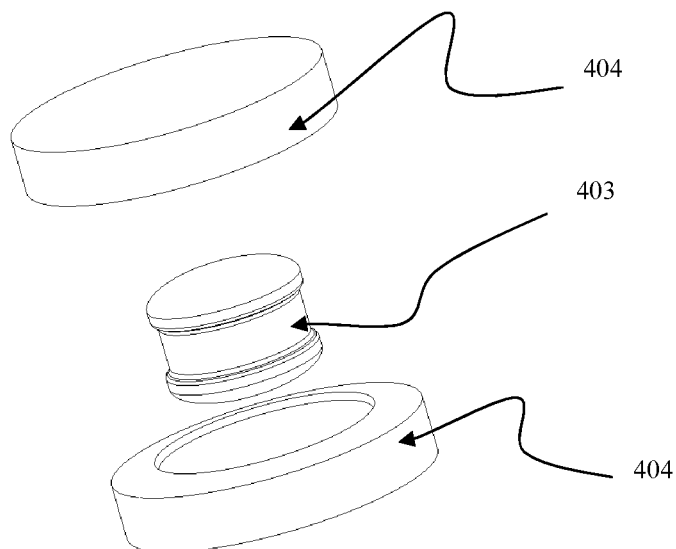
Figure 4B(1)
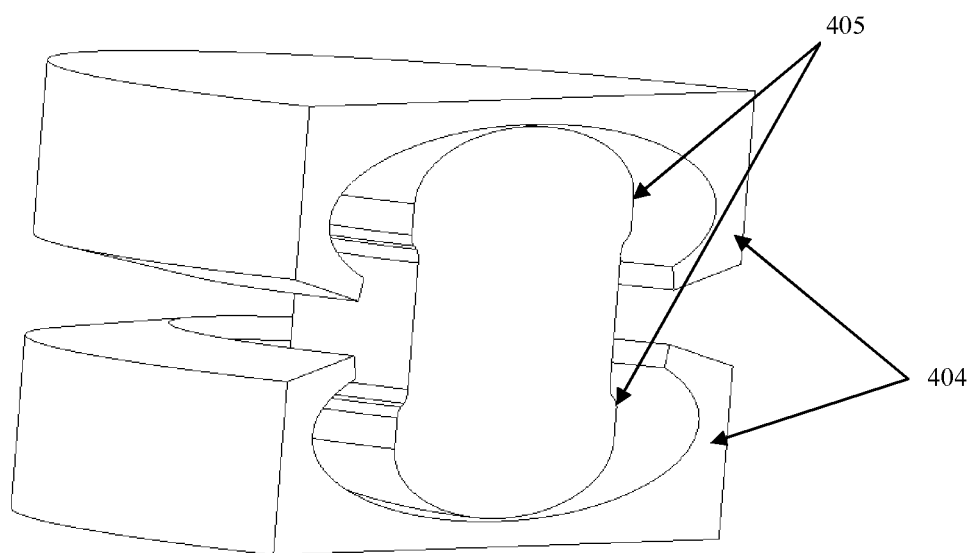
Figure 4B(2)

ARTIFICIAL DISC SYSTEM

This application is a Continuation of U.S. application Ser. No. 12/889,328, filed Sep. 23, 2010, which is a Divisional of U.S. application Ser. No. 11/487,415, filed Jul. 17, 2006, now U.S. Pat. No. 7,854,766, which claims priority of provisional application 60/788,720, filed Apr. 4, 2006; the entire contents of all the above identified patent applications are hereby incorporated by reference.

BACKGROUND OF THE INVENTION

1. Field of the Invention

The present invention relates to a posterior placed total lumbar artificial disc ("PTTLAD") without supplemental instrumentation, that uses removable bi-functional screws, sliding expansile plates, and interchangeable cores which enhance individualized custom-fitting. In addition, oblique plate traction spikes are used for enhanced vertebral endplate penetration and incorporation. The present invention also relates to artificial total lumbar discs which can be posteriorly introduced into the lumbar spinal intervertebral disc space, unilaterally, from either left or right side.

2. Description of the Relevant Art

Cervical and lumbar total artificial discs are entering the clinical neurosurgical and orthopedic markets. The benefits of these artificial discs are well known. They replace diseased discs, and preserve motion segment mobility. Discogenic and radicular pain are relieved without forfeiting segmental mobility, which is typical of traditional anterior or posterior lumbar fusions. Thus it is currently rational to place prosthetic discs anteriorly where access can be easily obtained, and they can be secured by a variety of anterior screw fixations. This technology is adequate for single level disc replacement in the cervical spine. However based on the current anterior cervical prosthetic disc screw fixation methodology its implantation is periodically complicated by screw failures e.g. partial or complete screw pullouts or breaks, and in most designs it is limited to single level replacement. Furthermore, for lumbar total artificial discs, placement is limited to only the L4/5 and L5/S1 disc spaces, and not above, secondary to aortic and vena caval anatomical restraints. Likewise, for the thoracic spine. Thus far no type of thoracic prosthetic disc device has been reported or described. Furthermore, despite the purported safety of placement of the current anterior total lumbar artificial discs, there is a significant risk of retrograde ejaculations in males, and the risk of vascular injury, which although small, is potentially catastrophic if it occurs.

The design of total artificial discs, which began in the 1970's, and in earnest in the 1980's, consists essentially of a core (synthetic nucleus pulposus) surrounded by a container (pseudo-annulus). Cores have consisted of rubber (polyolefin), polyurethane (Bryan-Cervical), silicon, stainless steel, metal on metal, ball on trough design (Bristol-Cervical, Prestige-Cervical), Ultra High Molecular Weight Polyethylene (UHMWPE) with either a biconvex design allowing unconstrained kinematic motion (Link SB Charite-Lumbar), or a monoconvex design allowing semiconstrained motion (Prodisc-Lumbar). There is also a biologic 3-D fabric artificial disc interwoven with high molecular weight polyethylene fiber, which has only been tested in animals. Cervical and lumbar artificial discs are premised on either mechanical or viscoelastic design principles. The advantages of mechanical metal on metal designs including the stainless steel ball on trough design and the UHMWPE prostheses include their low friction, and excellent wear characteristics allowing long term motion preservation. Their major limitation is the lack of elasticity and shock absorption capacity. The favorable features of the viscoelastic prosthetics include unconstrained kinematic motion with flexion, extension, lateral bending, axial rotation and translation, as well as its cushioning and shock absorption capacity. On the other hand, their long term durability beyond ten years is not currently known. Containers have consisted of titanium plates, cobalt chrome or bioactive materials. This history is reviewed and well documented in Guyer, R. D., and Ohnmeiss, D. D. "Intervertebral disc prostheses", Spine 28, Number 15S, S15-S23, 2003; and Wai, E. K., Se'mon, G. P. K. and Fraser, R. D. "Disc replacement arthroplasties: Can the success of hip and knee replacements be repeated in the spine?", Seminars in Spine Surgery 15, No 4: 473-482, 2003.

It would be ideal if total lumbar artificial discs could be placed posteriorly allowing access to all levels of the lumbar spine. Also one could place these devices posteriorly in thoracic disc spaces through a transpedicular approach. Similarly if these devices can be placed anteriorly particularly in the cervical spine without anterior screw fixation, and custom-fit it for each disc in each individual, the ease of placement would reduce morbidity and allow for multilevel disc replacement. Placement of an artificial disc in the lumbar spine if inserted posteriorly through a unilateral laminotomy by using a classical open microscopic approach or by using a minimally invasive tubular endoscopic approach would significantly reduce the possibility of recurrent disc herniation. If placed without facet joint violation, or with only unilateral mesial facetectomy, and the device can purchase the endplates with spikes there would be no need for supplemental posterior pedicle screw fixation, thus obviating the associated morbidity associated with pedicle screws and bone harvesting. To take it one step further, if artificial lumbar discs can be posteriorly placed successfully and safely throughout the entire lumbar spine, every routine lumbar discectomy could be augmented by artificial disc placement which would simultaneously eliminate discogenic and radicular pain while preserving flexibility. Furthermore by so doing, the probability of recurrent herniation plummets, and subsequently the need for posterior pedicle instrumentation plummets, thereby diminishing overall spinal morbidity, expenditure, and leading to the overall improvement in the quality of life.

Presumably up to now, technology is not focusing on posterior placement of total lumbar prosthetic discs because of inadequate access to the disc space posteriorly. To circumvent this problem others have been working on the posterior placement, not of a total prosthetic disc but of a prosthetic disc nucleus (PDN), or essentially a core without a container (pseudo annulus). PDNs, which are considered post-discectomy augmentations, have consisted of one of the following materials: 1) hydrogel core surrounded by a polyethylene jacket (Prosthetic Disc Nucleus). Two of these devices have to be put in. There is a very high, 38% extrusion rate, 2) Polyvinyl alcohol (Aquarelle), 3) polycarbonate urethane elastomer with a memory coiling spiral (Newcleus), 4) Hydrogel memory coiling material that hydrates to fill then disc space, 5) Biodisc consisting of in-situ injectable and rapidly curable protein hydrogel, 6) Prosthetic Intervertebral Nucleus (PIN) consisting of a polyurethane balloon implant with in-situ injectable rapidly curable polyurethane and 7) thermopolymer nucleus implant. (See the two publications identified above). The approach of posteriorly placing artificial disc cores appears to be flawed in that: 1) there is a high extrusion rate, 2) it lacks good fixation as does total prosthetic devices that are placed anteriorly, 3) it is restricted only to early symptomatically disrupted discs which have only nucleus pulposus but not annulus or endplate pathology, and 4) are contraindicated in discs with an interspace height of less than 5 mm.

The primary advantages of artificial disc placement include the replacement of diseased discs with prosthetic devices which mimic as much as possible healthy natural discs thereby relieving axial and radicular pain without forfeiting segmental mobility. There are currently in the orthopedic and neurosurgical markets FDA approved anteriorly placed artificial total lumbar discs. The major disadvantages of anterior placement of these devices include vascular injury, blood loss, and retrograde ejaculation in males.

In our previous copending patent application Ser. No. 11/019,351, filed on Dec. 23, 2004 and Ser. No. 10/964,633, filed on Oct. 15, 2004, which are herein incorporated by reference, we have described artificial expansile total discs for placement throughout the entire spine. The relevant history and prior art of artificial discs are summarized and reviewed there. The artificial discs described in our previous patent applications expand in two or three dimensions, and have internal expanding mechanisms which necessitate a bilateral surgical approach for posterior placement into the lumbar spine. In one embodiment of the present invention, we have simplified the design by omitting an internal expansion mechanism, and by having the one-pieced disc plates expand in only one direction. These modifications make it technically easy to place with minimal disruption of the normal spinal anatomy and with minimal morbidity. Currently in the spinal market there exist only anteriorly placed total artificial lumbar discs. The risks of the anterior placement of these discs are well known and documented, and include but are not limited by vascular injury and retrograde ejaculation. Their surgical removal if warranted is technically challenging and potentially fatal in extreme circumstances. Our design retains all the benefits of the anterior artificial disc with respect to motion preservation, and has none of the above mentioned risks. In addition we introduce an additional novel safety feature, ball limiters, which prevent extrusion of the ball from the artificial disc, and limit complete unrestrained motion.

BRIEF DESCRIPTION OF THE DRAWINGS

FIGS. 4A(1) and 4A(2) illustrate isometric and front views of the insertable core ball (Embodiment I).

FIGS. 4B(1) and 4B(2) illustrate exploded and cross-sectional views of an alternative ball/trough system (Embodiment II).

DESCRIPTION OF PREFERRED EMBODIMENTS

The Medical Device of FIGS. 1-7

Referring now to FIGS. 1-7, the above described problems can be solved in the lumbar spine by the posterior .insertion of a closed PPLTAD in the discs space after the performance of a discectomy. After insertion it is expanded in height (the anterior-posterior direction in a standing patient), and in width (disc space height in a standing patient).

Figure 1:
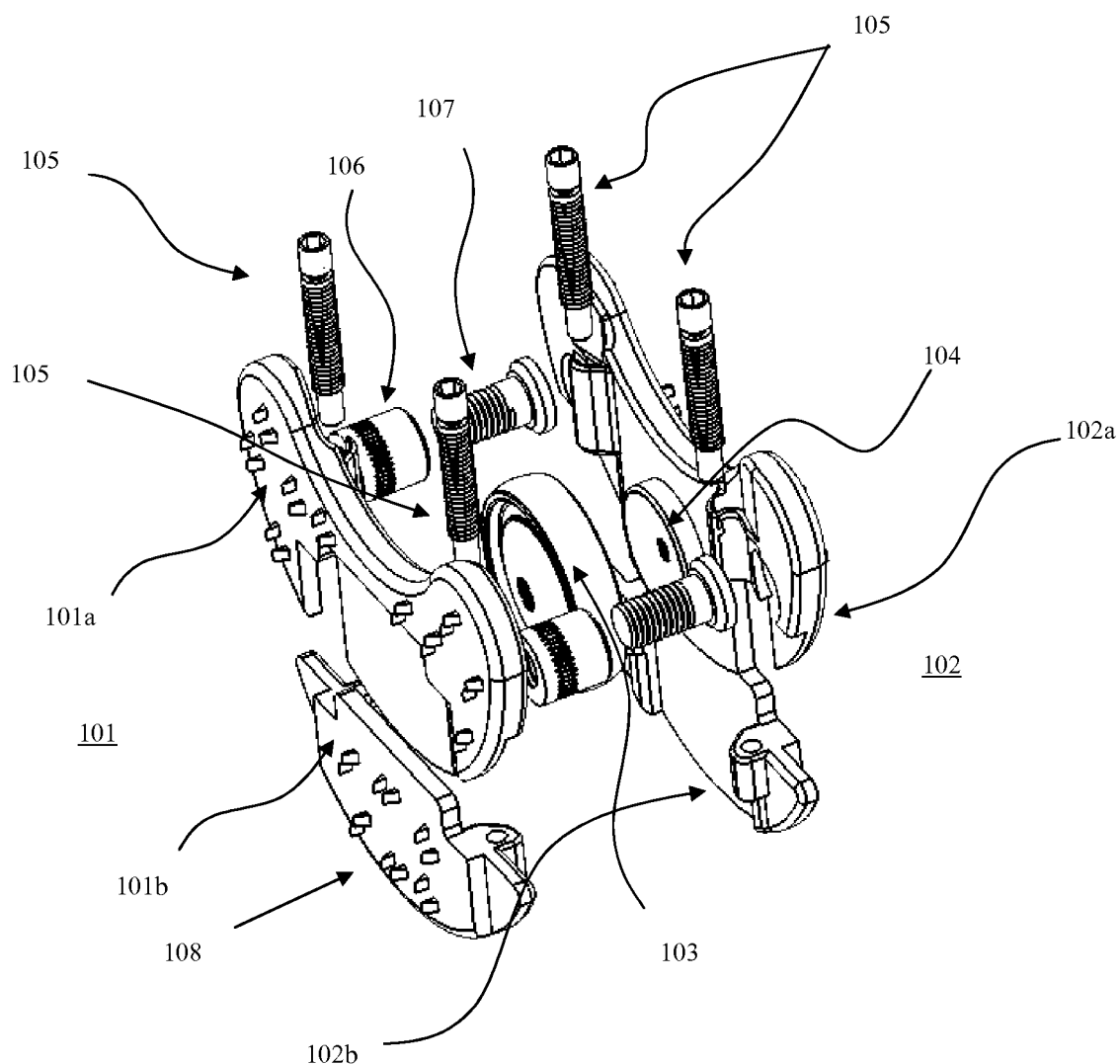
FIG. 1 illustrates an isometric exploded view of the posteriorly placed total lumbar artificial disc ("PPTLA").

FIG. 1 illustrates an isometric exploded view of the PPLTAD. It consists of two opposing plates 101, 102 which are preferably titanium or cobalt chromium, each of which is comprised of a dorsal component 101a, 102a and ventral component 101b, 102b. Sandwiched in between the opposing plates 101, 102 is a removable ball 103 which contacts a trough 104 on the inner aspects of both opposing plates.

The mechanical crux to the PPLTAD height and width expandability are based on the interaction of a bi-functional (height/width) adjustment (BFA) screw 105 with a slotted worm nut 106, and a width adjustment screw 107 and their unified interactions with the dorsal and ventral aspects of each the opposing plates 101, 102, and with their unified interaction with both opposing plates 101, 102.

Located on the outer aspects of the plates 101, 102 are a series of obliquely oriented spikes 108. The obliqueness of the spikes 108 hinders extrusion by orientation as well as by traction. We believe that this is a unique design which is not found in other prosthetic disc devices.

Figure 2:
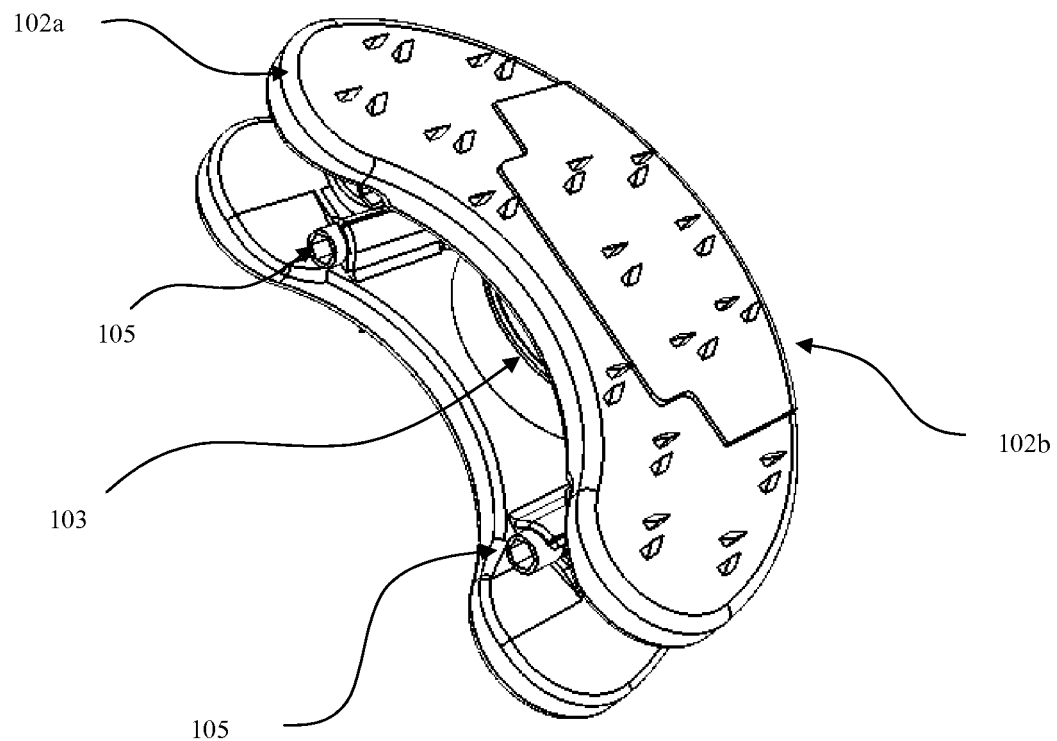
FIG. 2 illustrates an isometric view of the closed unexpanded PPLTA device.

FIG. 2 illustrates the PPLTAD in its closed position prior to its insertion into the empty disc space.

Figure 3:
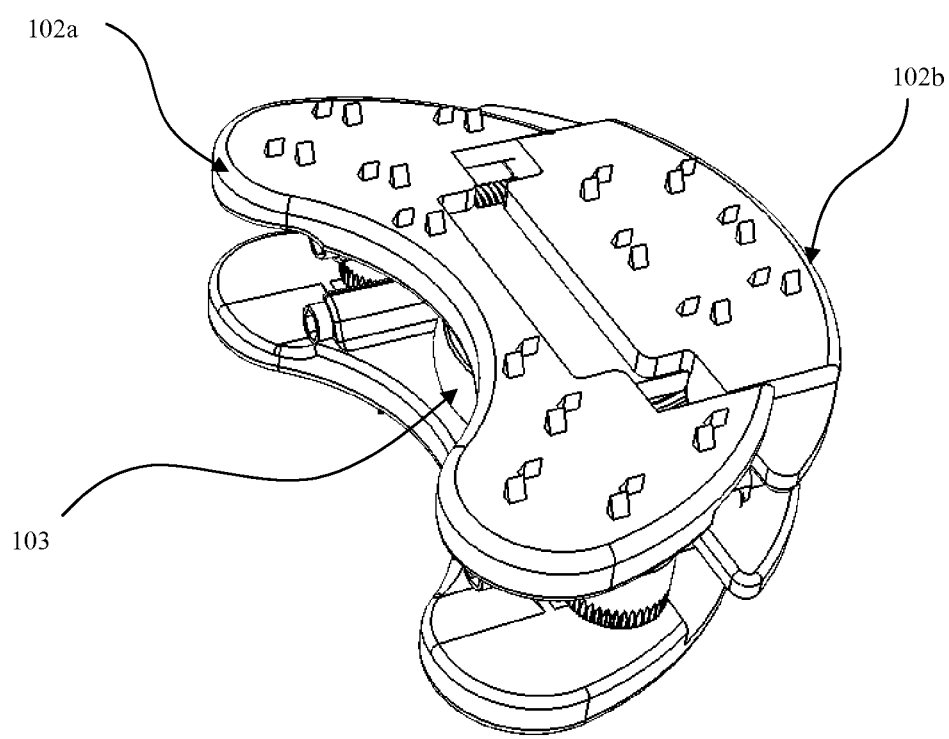
FIG. 3 illustrates an isometric view of the PPLTA device with anterior plate expansion (extension).

FIG. 3 illustrates the PPLTAD with an extended (expanded) ventral plate 102b.

FIGS. 4A(1) and 4A(2) illustrate isometric and frontal views respectively of the ball insert 103 (Embodiment I). It consists of an ellipsoid core 401 surrounded by a raised edge 402. Upon its insertion into the PPLTAD when both surfaces of the ball 103 contact the troughs 104 of the opposing plates 101, 102 and moves within them, the raised edge 402 prevents ball extrusion with patient movement.

FIGS. 4B(1) and 4B(2) illustrate a different ball/trough embodiment (II). In this embodiment it is the ensconcing trough protrusions 404 surrounding the ball 403 and ball overhangs 405 which prevent ball extrusion as opposed to the ball rim (Embodiment I) preventing ball extrusion. This preferably allows for the same degree of lateral flexion and rotation as Embodiment I.

Figure 5A:
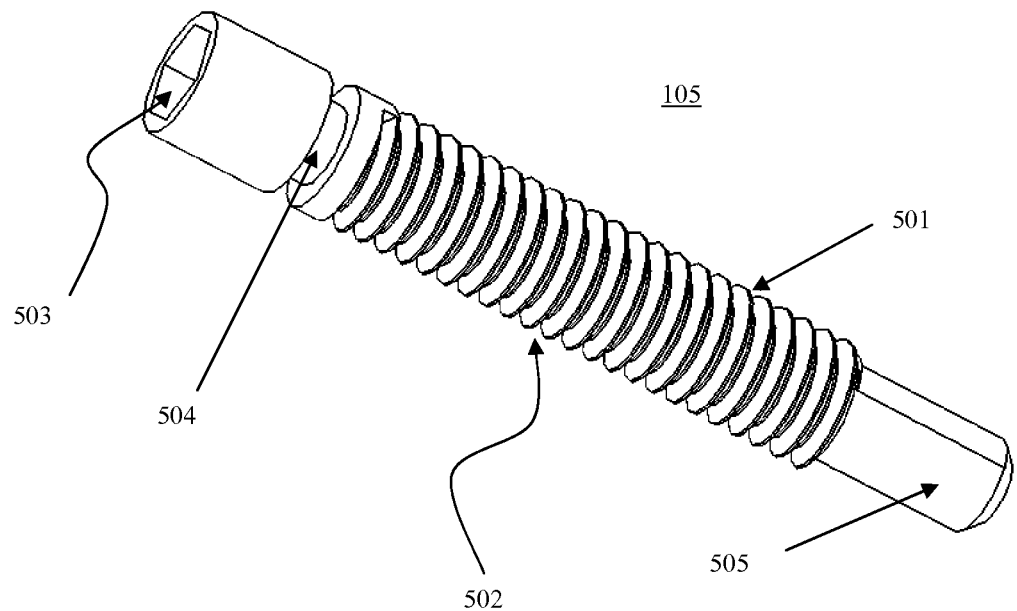
FIGS. 5A, 5B and 5C illustrate the components which act in unison to allow width and height device expansion. They include the bi-functional (height/width) adjustment (BFA) screw (5A), the width adjustment screw (5B), and the intervening slotted worm nut (FIG. 5C).
Figure 5B:
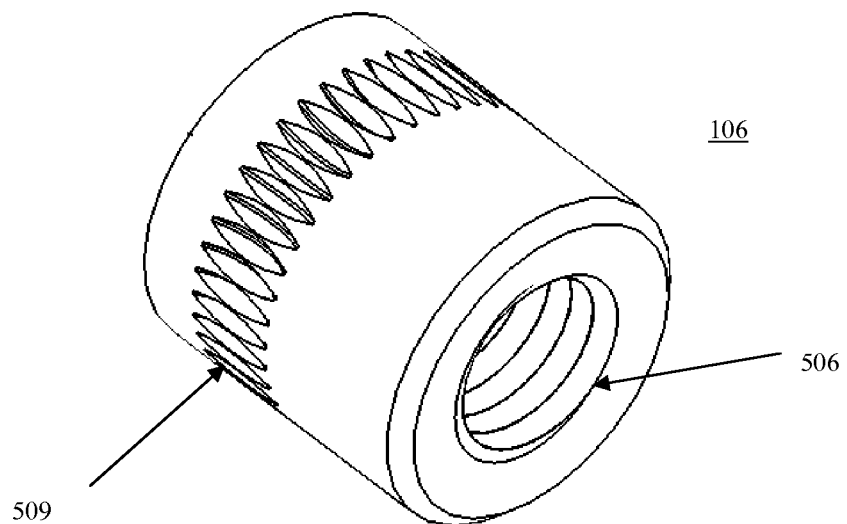
Figure 5C:
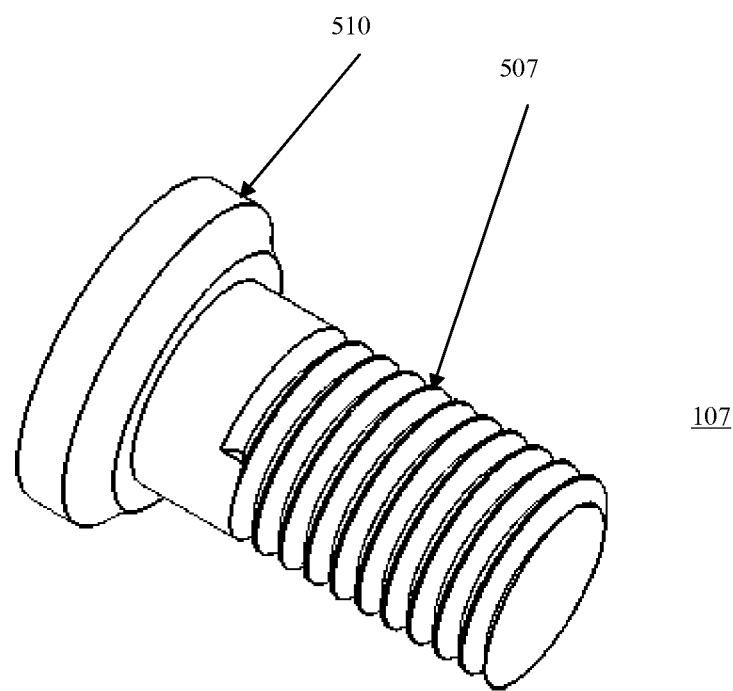

FIGS. 5A, 5B and 5C illustrate close up views of the key components of the expansile mechanism. FIG. 5A illustrates a close-up of the bi-functional (height/width) adjustment (BFA) screw 105. It is composed of a screw body 501 with threads 502, a hex slot 503, a neck 504 and a collar 505. This screw 105 is inserted into the open bearings 601 of the inner aspect dorsal plate 102a (FIGS. 6B and 6C) and the height adjustment threaded nut 704 and slot 703 of the inner aspect of the ventral plate 102b (FIG. 7B).

The BFA threads 502 of screw 105 are in direct contact with the external slots 509 of the slotted worm nut 106 (FIG. 5B, and FIG. 1). The slotted worm nut 106 in turn has internal threadings 506 (FIG. 5B) which accommodate the external threading 507 of the width adjustment screw 107 (FIG. 5C, FIG. 1). The countersunk head 510 of the width adjustment screw 107 (FIG. 5C), and the head of the slotted worm nut 106 fit into corresponding slots 602 on the inner aspect of the opposing dorsal plates 102a (FIG. 6B).

Figure 6A:
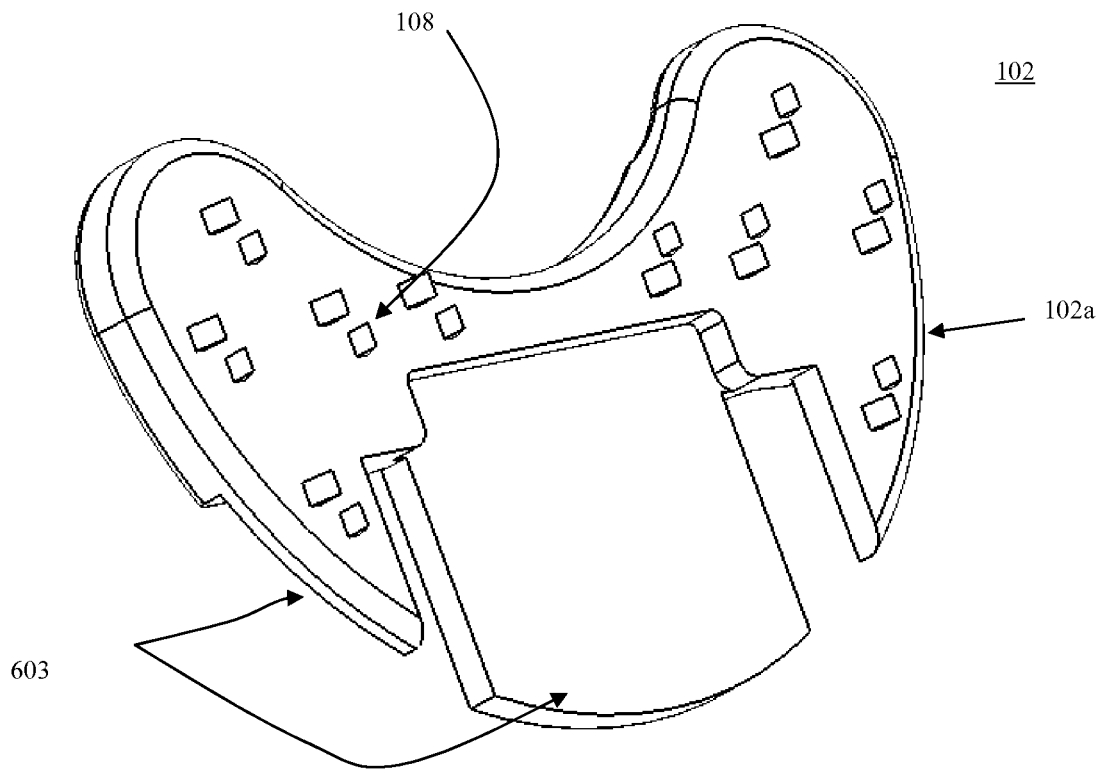
FIGS. 6A and 6B illustrates the external (FIG. 6A), internal (FIG. 6B), and top (FIG. 6c) views of the dorsal plate.
Figure 6B:
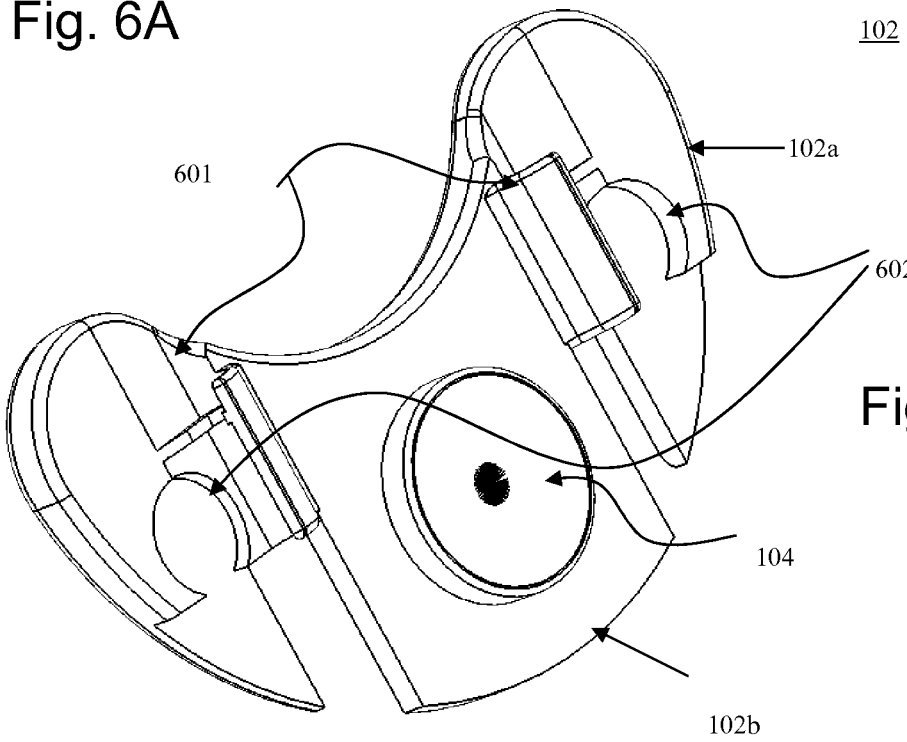
Figure 6C:
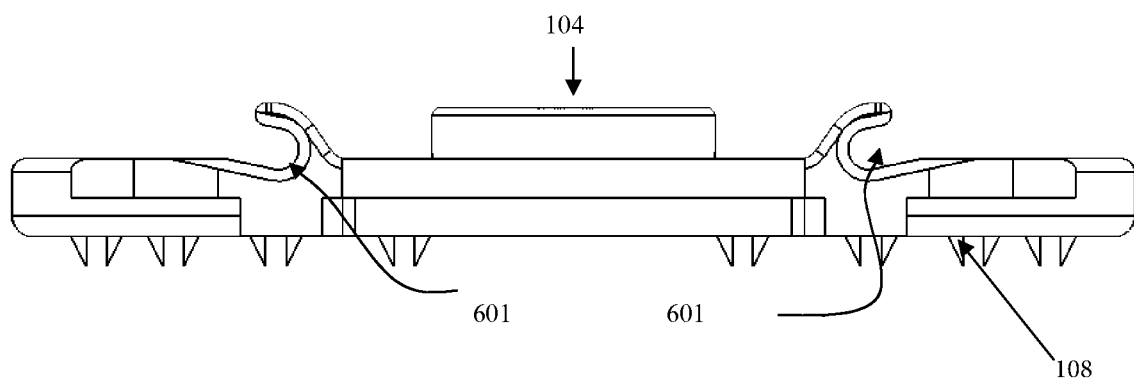
Figure 7A:
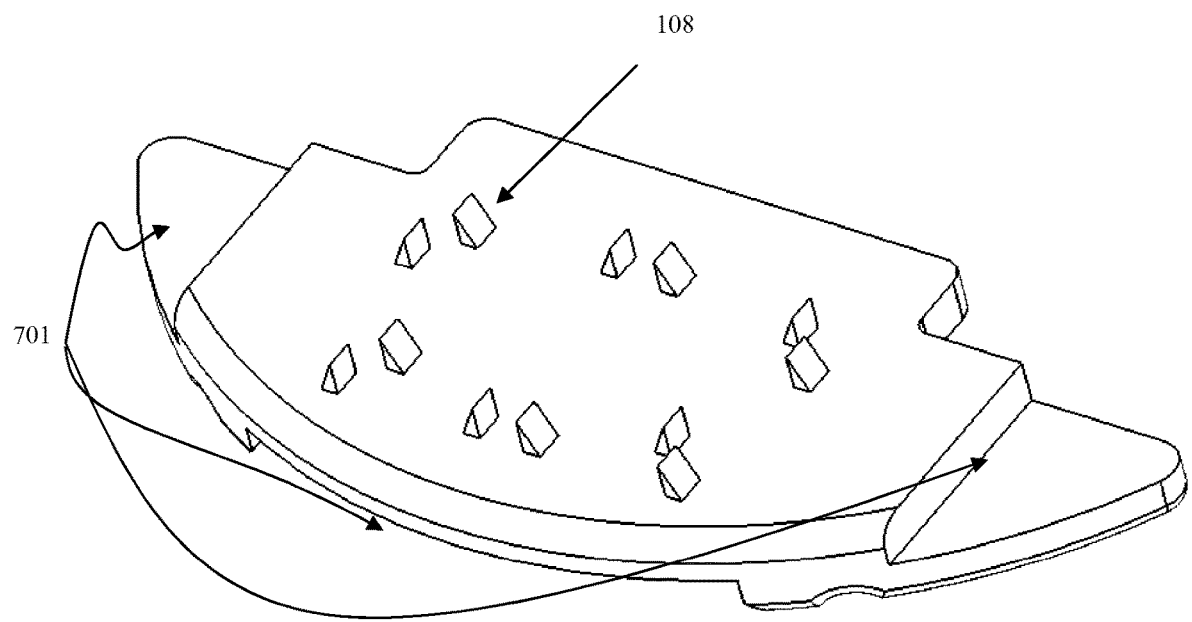
FIGS. 7A and 7B illustrate the external (FIG. 7A) and internal (FIG. 7B) views of the ventral plate.

FIGS. 6A, 6B, 6C, 7A and 7B illustrate a variety of views of the dorsal and ventral plates 102a, 102b. They illustrate their interrelationship, and their connectivity. The external view of the dorsal plate 102a (FIG. 6A) illustrates a large mid-line flange, and positioning flanges 603 on its left and right, which insert into the ventral plate slots 701 for the dorsal flanges (FIG. 7A). FIG. 6B illustrates the internal aspect of the dorsal plate 102a. This has the trough 104 in a fixed position, and the open bearings 601 for insertion of the BFA screws 105. It also illustrates the slots 602 for either the width adjustment screws 107 or the worm nuts 106 in the opposing plates. FIG. 6C is a top view of the dorsal plate 102a illustrating the open bearings 601 for the BFA screws 105, the spikes 108 and the trough 104.

Figure 7B:
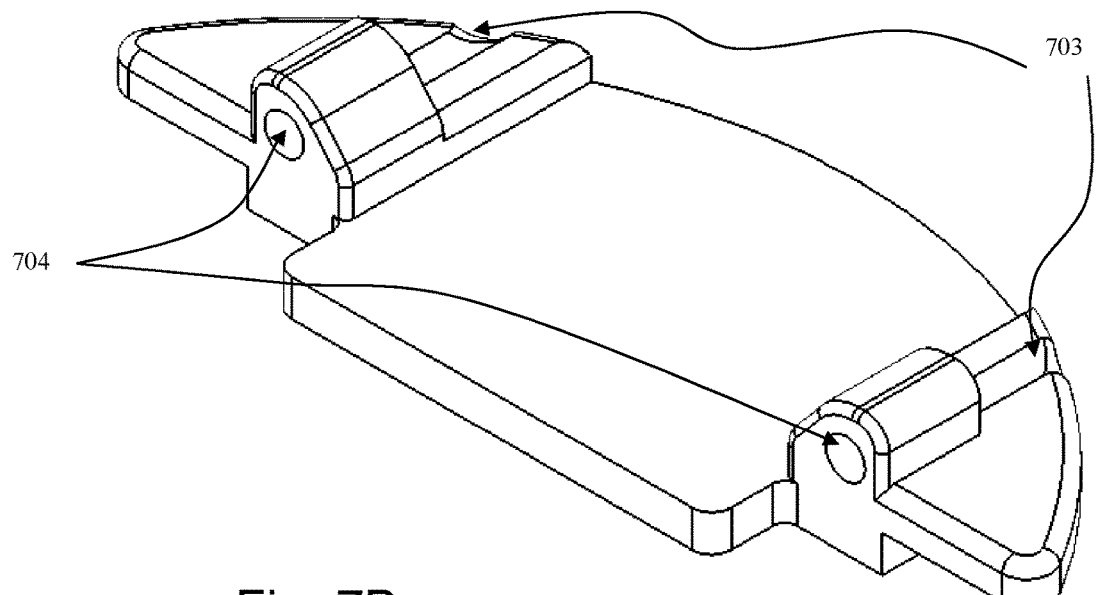

FIG. 7B illustrates the threaded nuts 704 into which the BFA screws 105 are inserted as well as their slots 703 which the bottom aspect of the BFA screws 105 rest upon.

Another possible embodiment of the opposing plates includes making the opposing plates different sizes, and decreasing the sizes of the screws, thus allowing even more lateral flexion.

We will now describe the mechanism of height and width expansion. The closed PPLTAD is inserted into the emptied disc space (FIG. 2). The height is expanded by turning each of the four BFA screws 105 (FIG. 1). These screws 105 by virtue of being inserted into the height adjustment threaded nuts 704 of screws of the ventral plate 102b (FIG. 7B), and the open bearings 601 of the dorsal plate 102a (FIG. 6C), allow graded sliding of the ventral plate slots 703 vis-a-vis the dorsal plate flanges 603 hence achieving graded separation from each other, i.e. height expansion (FIGS. 1, 3, 6A and 7A). When maximum desired height is achieved, further turning of the BFA screws 105 rotate the worm nut 106 which then drives the width adjustment screw 107 against the opposing plate thereby leading to opposing plate separation thus driving the opposing plates 101, 102 into the opposing vertebral endplates via the spikes 108 (FIG. 1). Once the plates 101, 102 are engaged in the vertebral endplates via spike 108 penetration and incorporation, the BFA screws 105 are turned counter-clockwise thereby disengaging them from the inner aspects of the plates 101, 102, and the slotted worm nuts 106. The BFA screws 105, slotted worm nuts 106 and width adjustment screws 107 are now removed, having performed their jobs of height and width expansion. It is necessary to remove these objects so that the inner ball core 401 may interact with the inner troughs 104 and achieve complete and unhindered flexibility of motion. Different sized ball inserts 401 accommodate for differences in disc space height. Thus once the plates 101, 102 of the PPLTAD are inserted and driven into the endplates, the disc height is measured, and the appropriately fitted ball 401 is inserted to precisely fit the distance of separation between the opposing troughs 104. This maximizes function, and minimizes extrusion.

The Surgical Method of FIGS. 1-7

The method of posterior insertion of the PPLTAD into the posterior interspace can be performed open microscopically, or closed tubularly, using endoscopic and/or fluoroscopic guidance.

After the adequate induction of anesthesia the patient is positioned in the prone position. A midline incision is made, bilateral lamina are exposed, and bilateral hemi-laminotomies are performed preserving bilateral facet joints so as not to incur instability.

A complete discectomy is performed and the superior and inferior endplates exposed. The closed PPTLA without the core ball 401 is inserted. The four BFA screws 105 are turned clockwise leading to height extension of the opposing plates 101, 102 via downward sliding of the ventral segments 101b, 102b of the plates. The screws 105 are turned further clockwise thereby turning the width adjustment screws 107 via the turning of the slotted worm nut 106. This drives the opposing plates 101, 102 with their outer plate spikes 108 into the ventral endplates securing their attachment to the vertebral endplates. Fluoroscopic guidance is used to verify placement of the troughs 104 of the inner aspect of the plates 101, 102 at the center of the endplates so that they are at the center of gravity. Once the plates are secured into position the BFA screws are turned counter-clockwise, thereby disengaging from the plates 101, 102 and the worm nuts 106. Once disengaged, the BFA screws 105 are removed from their slots, and the slotted worm nuts 106 and widening screws 107 are disengaged from their inserts. We now have two opposing plates 101, 102 with their opposing inner troughs 104 engaged in two opposing vertebral endplates. The size between the opposing troughs 104 is measured, and a custom-sized ball 401 is now inserted in between the troughs 104. The size of the ball 401 is such that it will fit substantially perfectly, and hence not dislodge. The patient is now closed in routine manner.

This device and method of insertion offer safe posterior lumbar placement with equal motion preservation compared to anteriorly placed lumbar discs. This PPLTAD can also be adopted for anterior lumbar placement, and for posterior and anterior placement into thoracic disc interspaces. In our previous patent we have a modified plate shape for anterior cervical disc placement. The mechanism described herein is easily adapted for cervical artificial discs that do and don't expand in height. We believe this PPLTAD treats disc disease with significantly decreased morbidity compared to other current devices, whilst preserving spinal segmental flexibility, and enhancing quality of life.

The Medical Device of FIGS. 8-19

Figure 8:
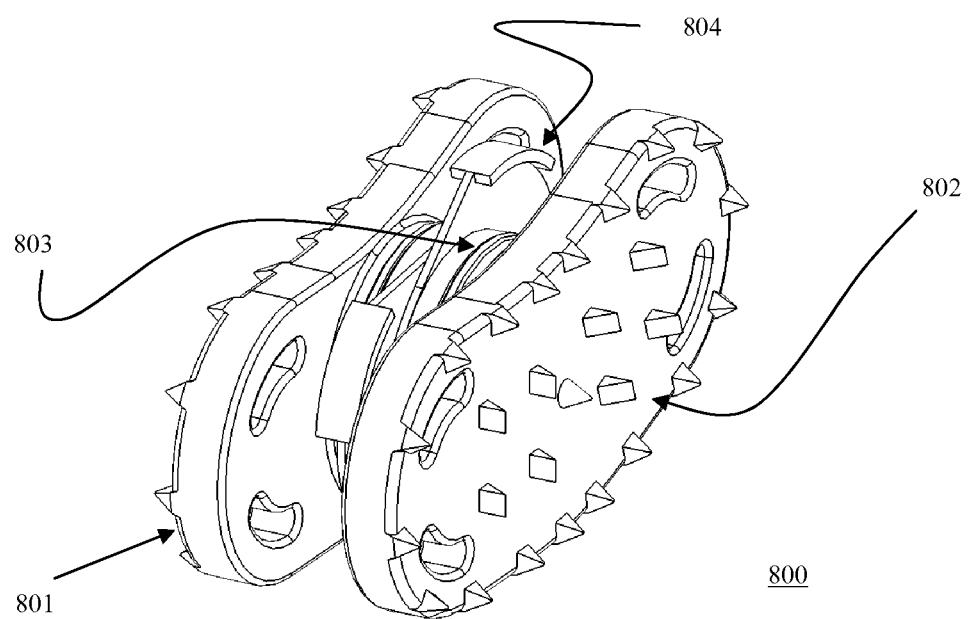
FIG. 8 illustrates an orthographic view of the uni-dimensional expanding artificial disc, embodiment I (UDEAD I).
Figure 9:
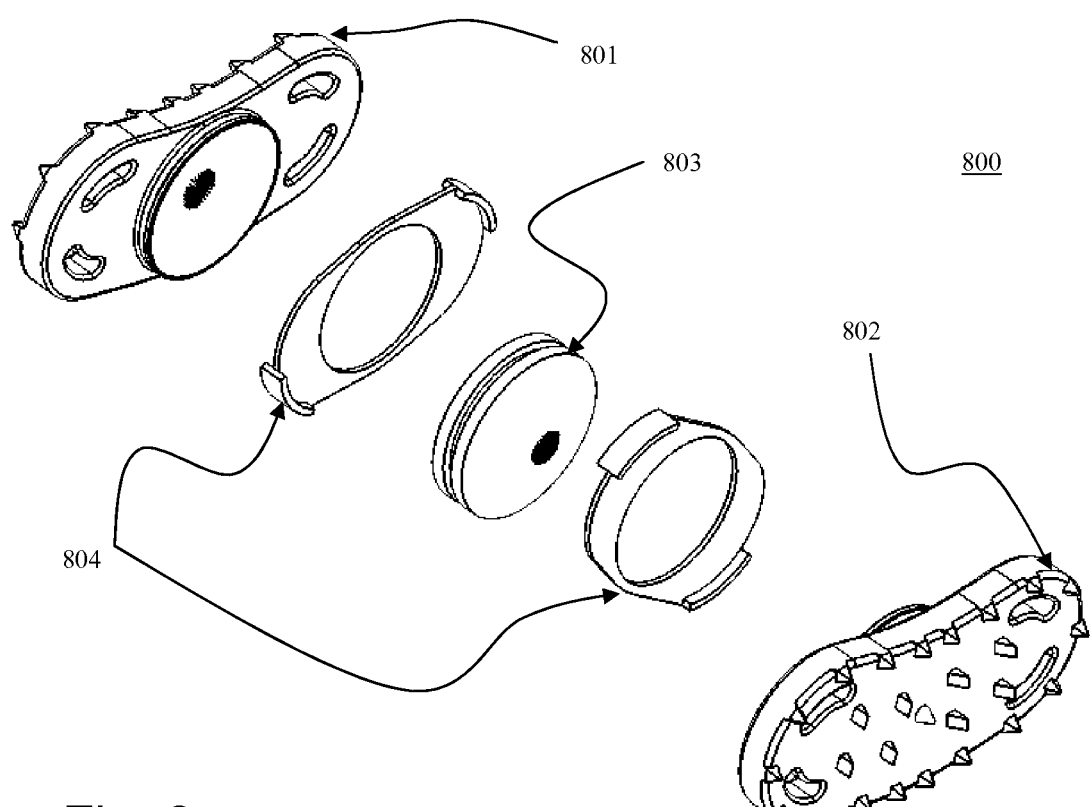
FIG. 9 illustrates an exploded view of the artificial disc (UDEAD I).

Referring now to FIGS. 8-19, the above described problems can also be solved by inserting a total artificial disc 800 which consists of three separate components; two opposing bean shaped plates 801, 802 and an interposing ball 803 which has ball limiters 804 which prevent ball extrusion (embodiment I), or raised edges which prevent extrusion (embodiment II). FIGS. 8 and 9 illustrate orthographic and exploded views of the artificial disc 800 (embodiment I). FIGS. 15A-C illustrate the orthographic, frontal and exploded views of Embodiment II. FIGS. 16A and B illustrate the side and orthogonal views of the ball of embodiment II.

Figure 10A:
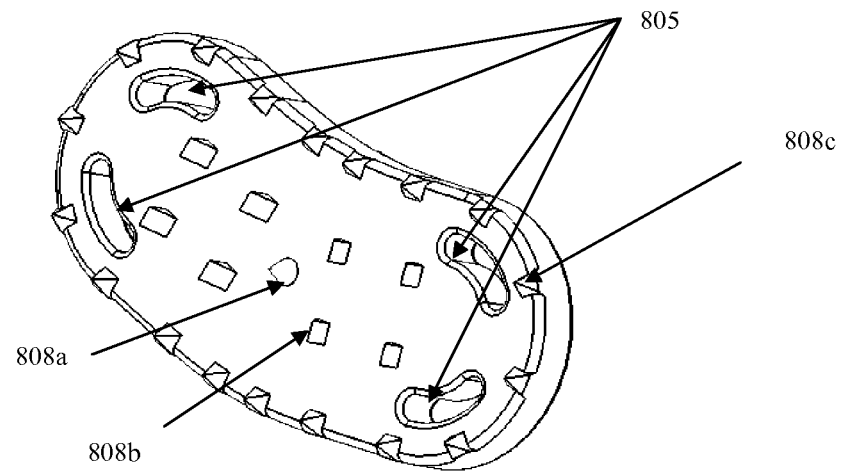
FIGS. 10A and 10B illustrate the external and internal views of the external plates of the artificial disc (UDEAD I).

FIG. 10A illustrates the external view of either the superior or interior plates 801, 802 (embodiments I and II). On the external surface of the plate 801 there are three types of spikes 808 to facilitate penetration and integration into the vertebral endplates. There is one conical center spike 808a. Around the peripheral edge of the plate 801 are multiple pyramidal spikes 808c. Surrounding the conical spike are right angled lateral spikes 808b. Each of the three types of spikes 808 is designed to facilitate penetration contoured to the shape of the plate 801 with respect to the vertebral endplate. We are not aware of any other artificial disc designs which have this feature. Also illustrated are the alignment slots 805 which align with an external insertion/spreading device 1500 (FIGS. 18-19).

Figure 10B:
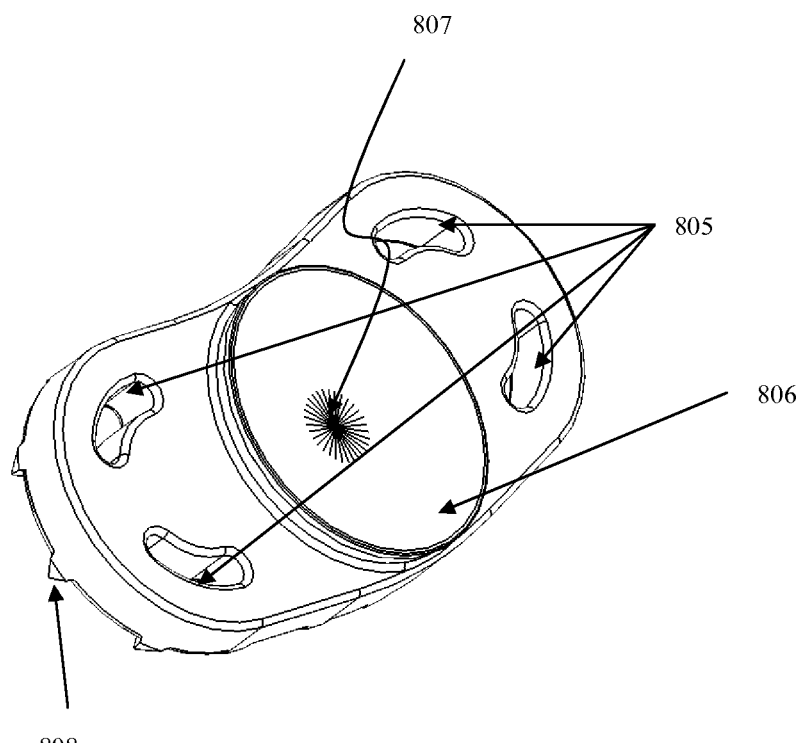

FIG. 10B illustrates the internal view of the superior or inferior plate 801. Centrally located is a trough 806 which will interact with the ball 803 of this ball/trough designed artificial disc. At the center of the trough 806 are radial grooves 807 which interact with similar radial grooves 1100 of the ball 803 (FIG. 11B 15C) facilitating ball/trough contact.

Figures 11A, 11B:
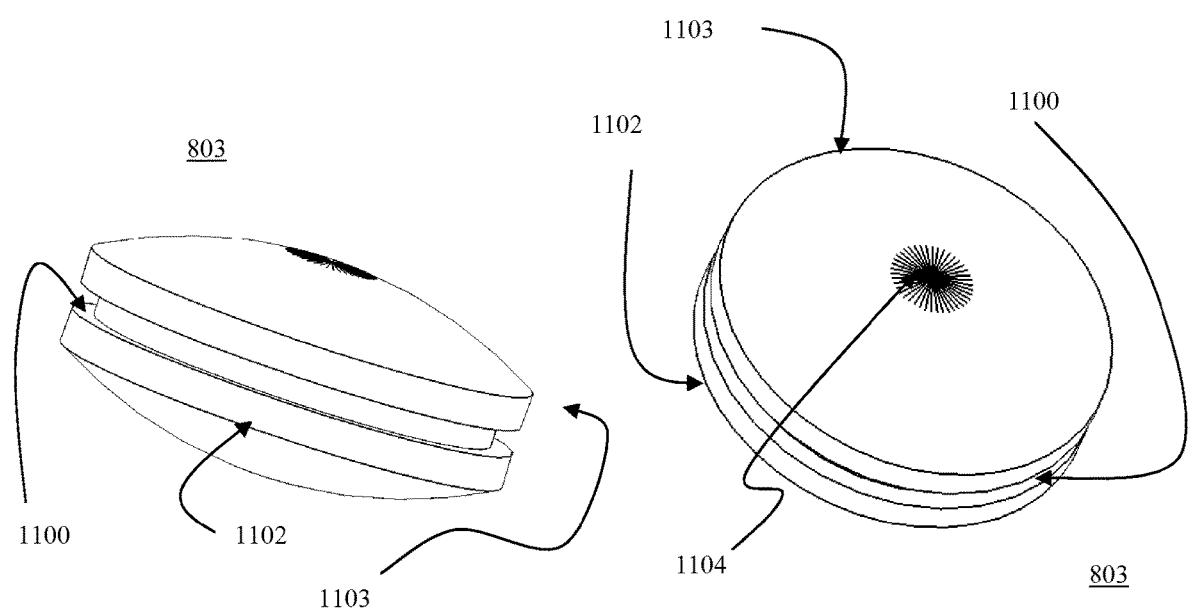
FIGS. 11A and 11B illustrate the side and orthographic views of the ball of the artificial disc UDEAD I).
Figure 12A:
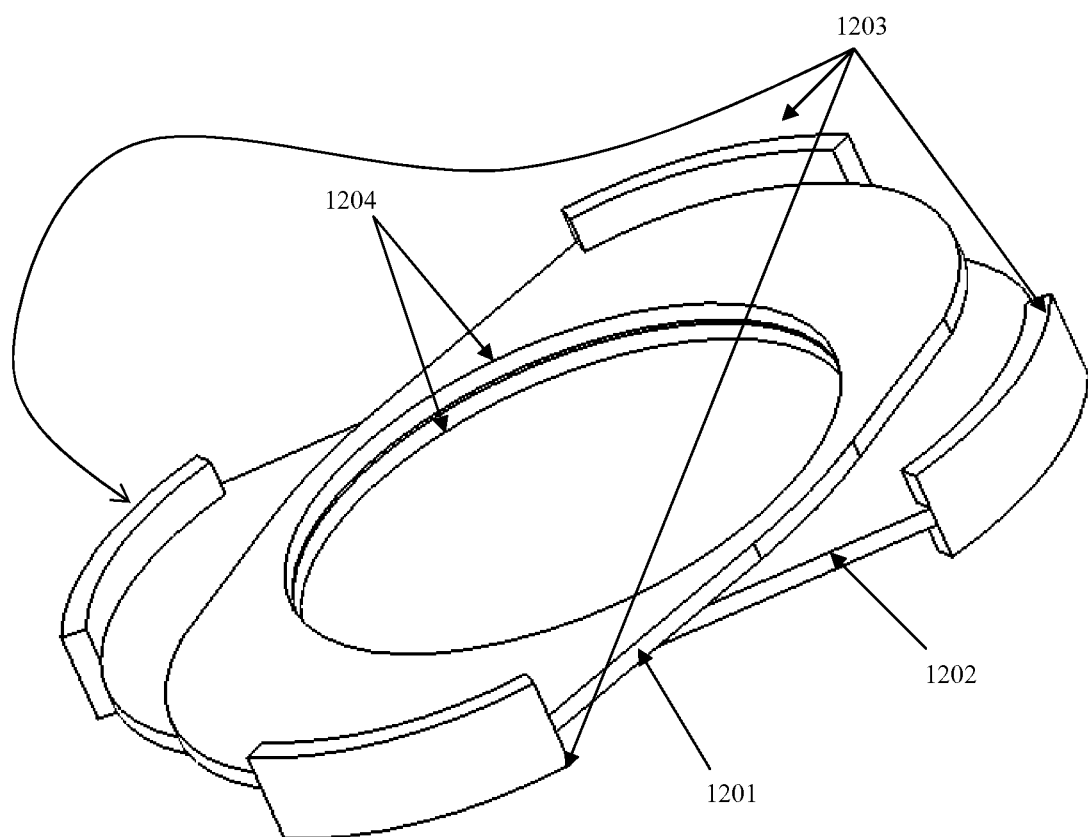
FIGS. 12A and 12B illustrate the orthographic and exploded views of the ball limiters (UDEAD I).
Figure 12B:
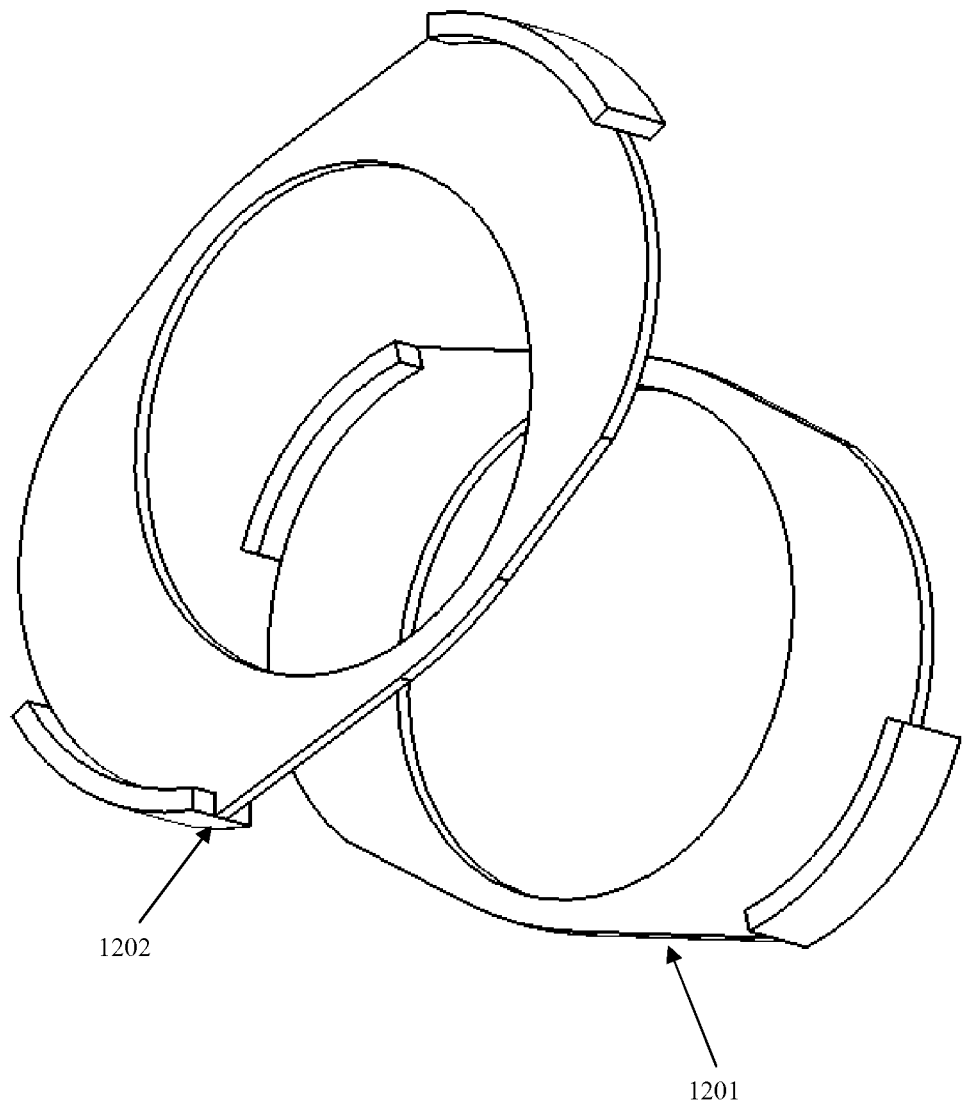
Figure 13:
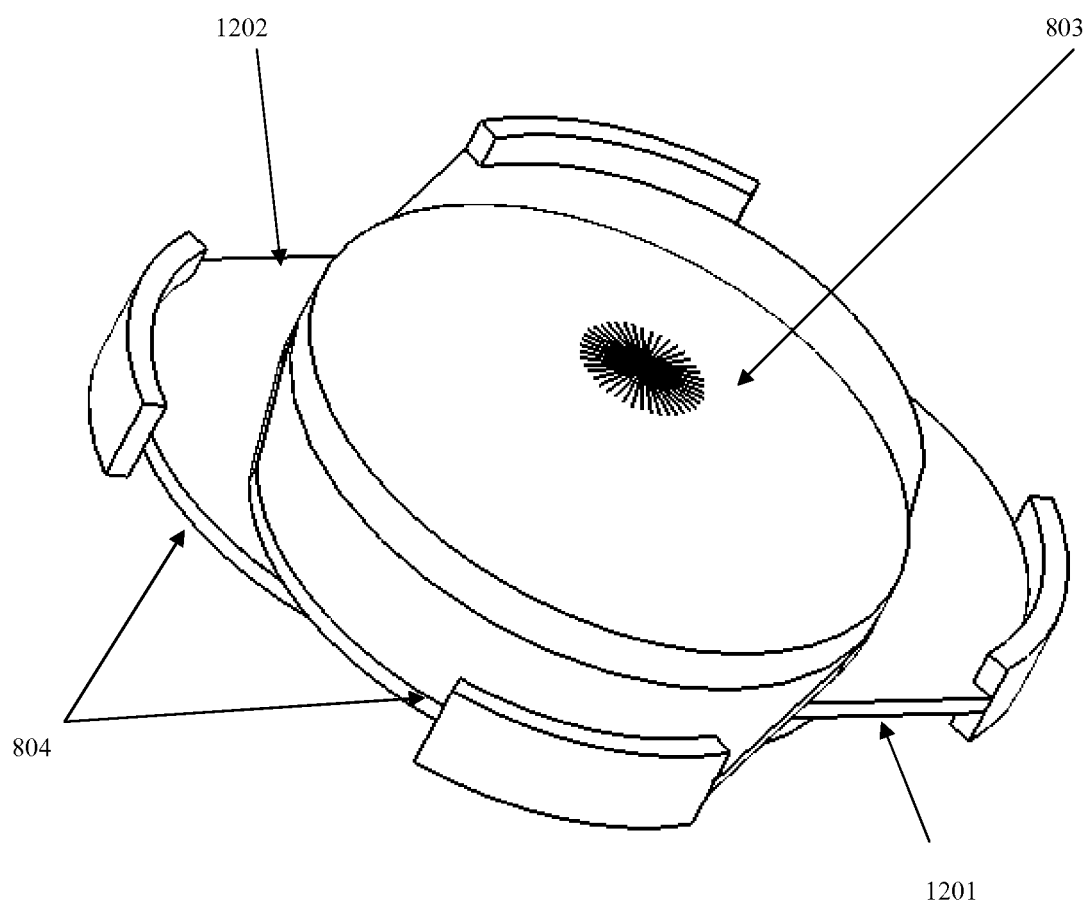
FIG. 13 illustrates the ball with the limiters (UDEAD I).
Figure 14:
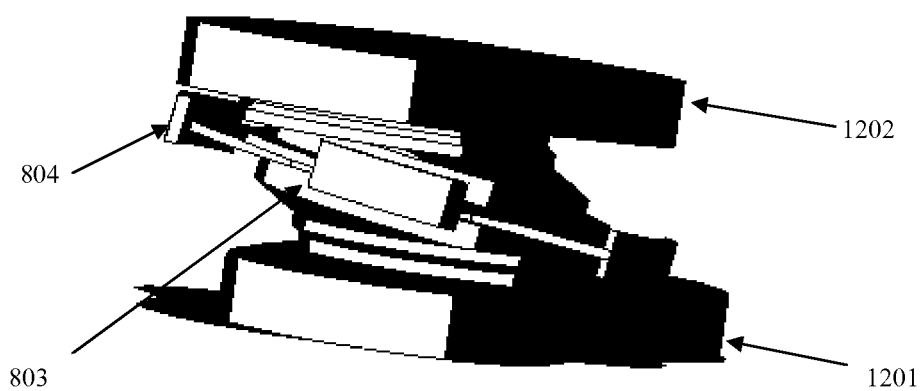
FIG. 14 illustrates a sample position of the entire artificial disc and how the ball limiters affect range of motion (UDEAD I).

FIGS. 11A and 11B illustrate the ball 803 design (embodiment I). It has superior and inferior domes 1102, 1103. In between the domes 1102, 1103 is a groove 1100 for the ball limiters 804. The ball limiter 804 inserts into the ball groove 1100 (FIGS. 11 and 13). FIG. 12 illustrates that the ball limiter 804 is composed of superior and inferior leaflets 1201, 1202. At the periphery of these leaflets 1201, 1202 there are raised barriers 1203 which limit ball motion and extrusion. After the plates 801, 802 are inserted, when the ball 803 and limiters 804 are introduced, the superior and inferior leaflets 1201, 1202 are aligned with each other. The inferior leaflet 1201 preferably includes a ball groove insertion ring 1204. After the ball 803 is inserted the ball limiters 804 are rotated such they are at approx 45-90 degrees angled with respect to each other (FIGS. 12A and 13). FIG. 14 illustrates a sample position of the artificial disc 800. It should be noted that with flexion and translation of the device 800, the raised barriers 1203 of the ball limiters 804 are in contact with the superior and inferior plates 801, 802 thereby limiting unrestrained motion of the ball 803, and prevents ball extrusion.

Figure 15A:
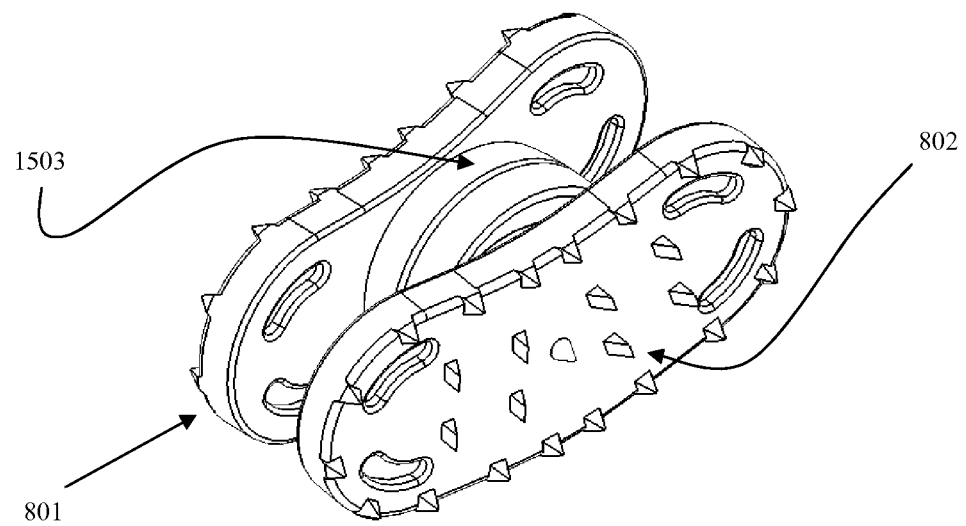
FIGS. 15A, B, and C illustrate the orthographic, frontal and exploded views of yet another embodiment of the UDEAD (embodiment II) which employs a ball with raised edges instead of ball limiters.
Figure 15B:
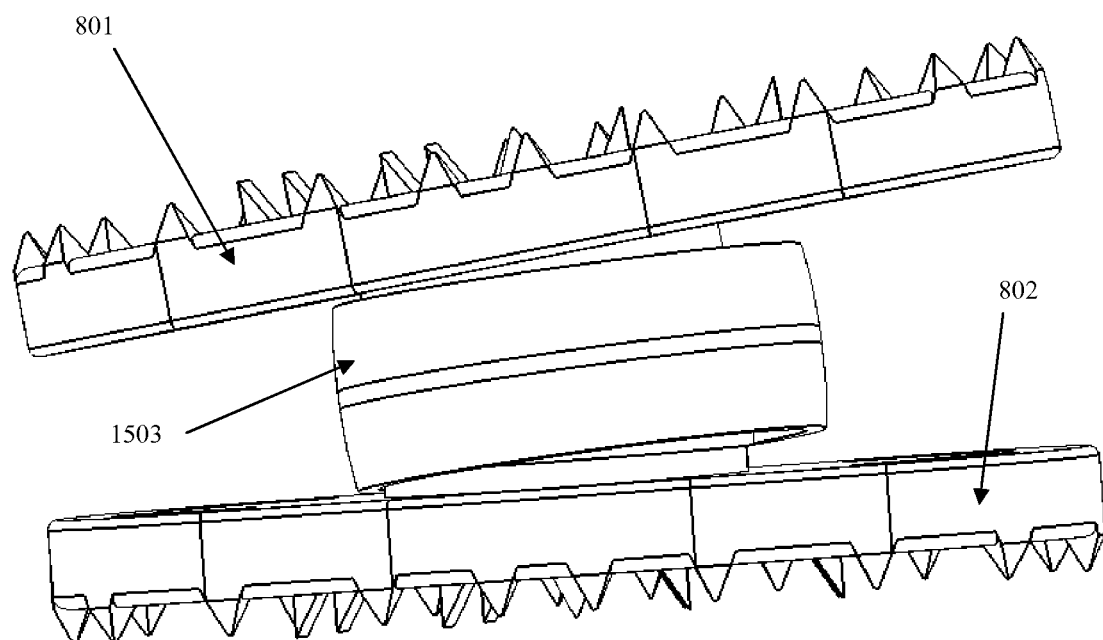
Figure 15C:
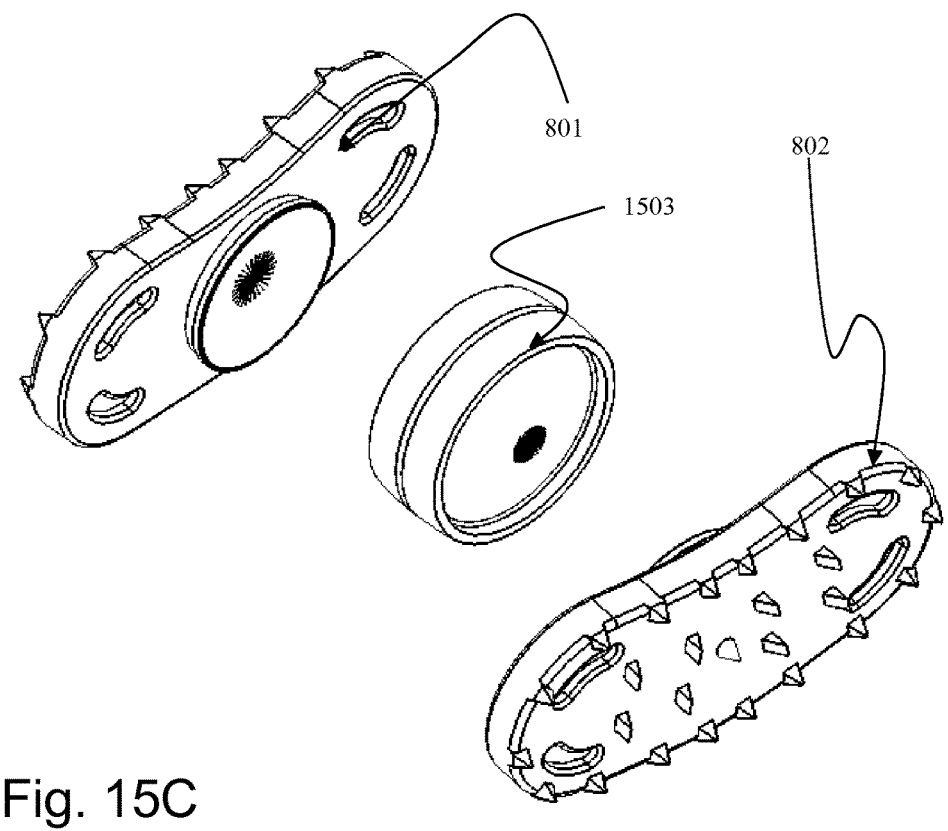

FIGS. 15A, B and C illustrate orthographic, frontal and exploded views of embodiment II. In FIGS. 15A, B and C, a ball 1503 is disposed between superior plate 181 and inferior plate 802.

Figure 16A:
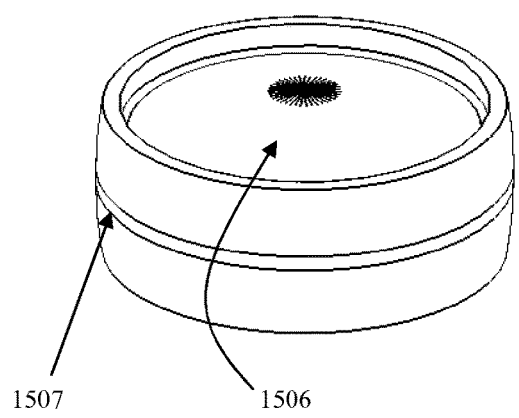
FIGS. 16A and 16B illustrate side and orthographic views of the ball employed in UDEAD II.
Figure 16B:
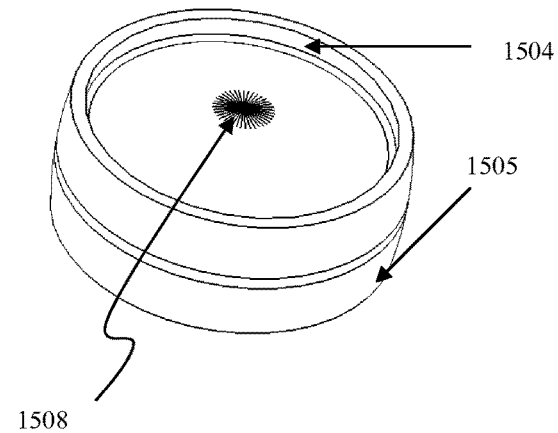

FIGS. 16A and 16B illustrate the side and orthographic views of the ball of UDEAD (embodiment II). The ball 1503 preferably includes a groove 1507 for radiographic material, superior dome 1506, and inferior dome (not shown). The ball 1503 also includes superior raised edge 1504, inferior raised edge 1505 and radial grooves 1508. This ball has raised edges instead of limiters which prevent its extrusion and unrestrained motion.

Figure 17A:
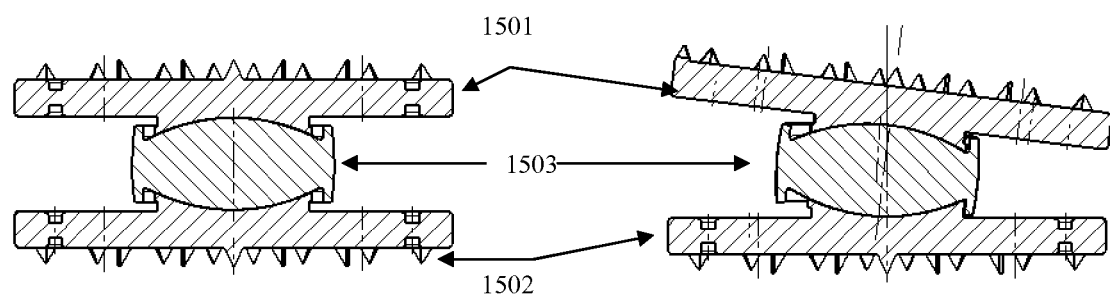
FIGS. 17A and 17B illustrate cross-sections of UDEAD (embodiment II) during lateral bending and flexion/extension.
Figure 17B:
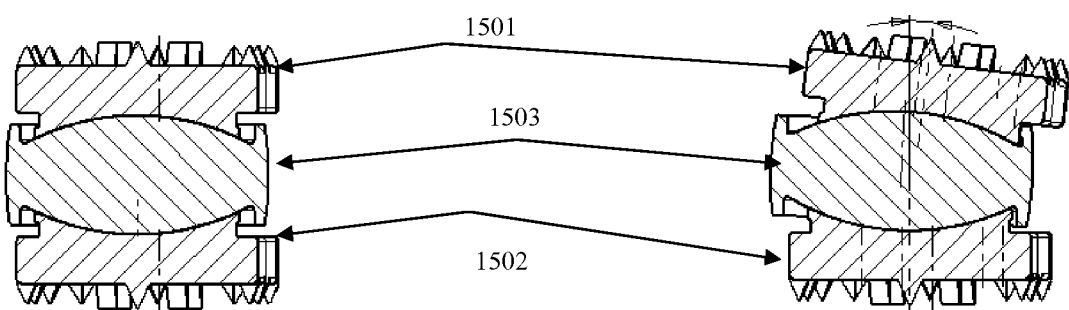

FIGS. 17A and 17B illustrate the motion of the ball insert during lateral bending, and flexion/extension.

Figure 18A:
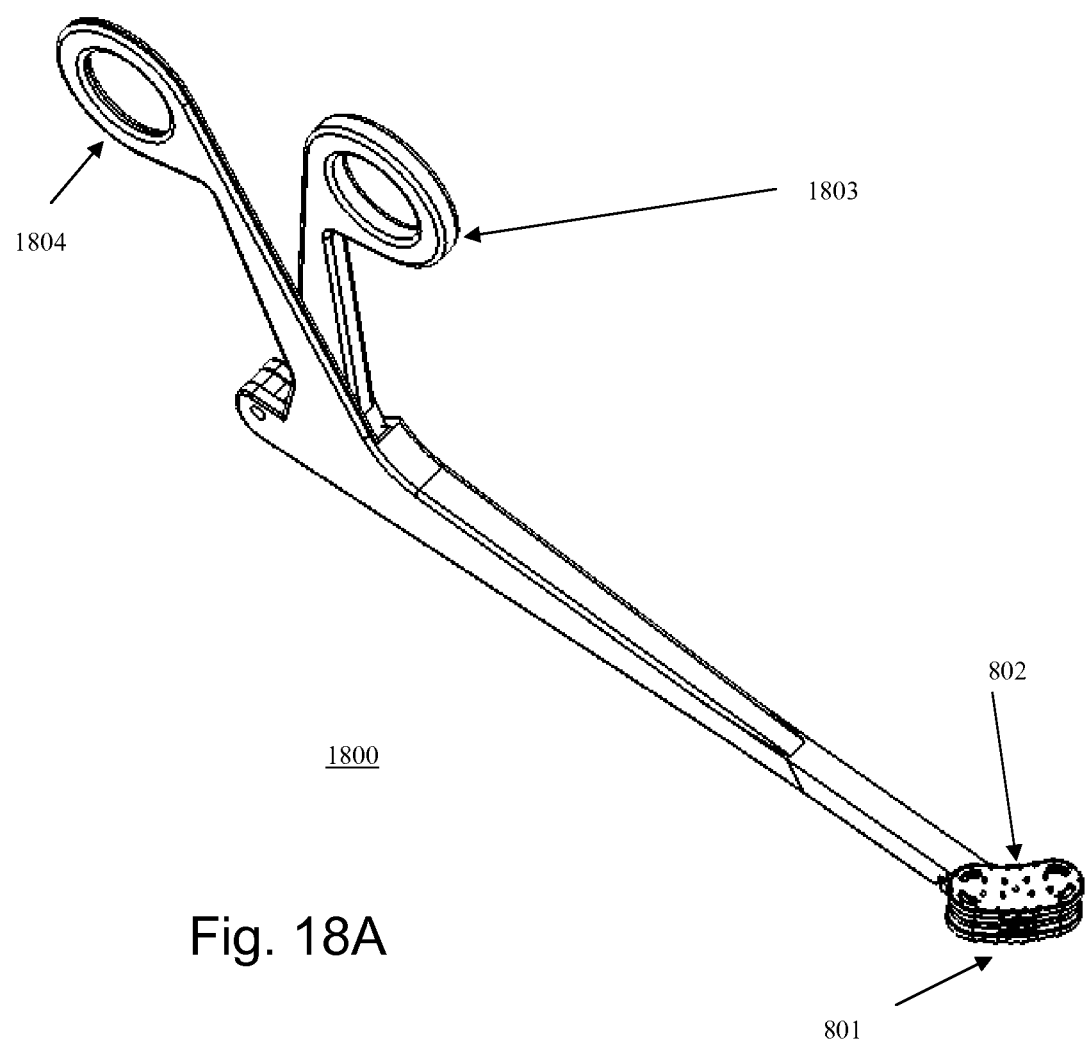
FIGS. 18A, 18B and 18C illustrate the front, back and exploded views of the external insertion device used for UDEAD embodiments I and II.
Figure 18B:
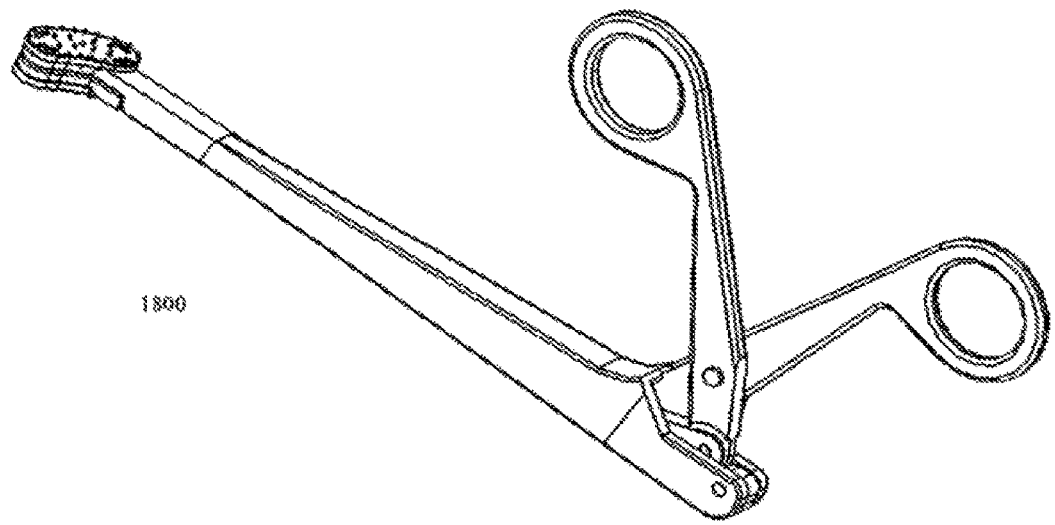
Figure 18C:
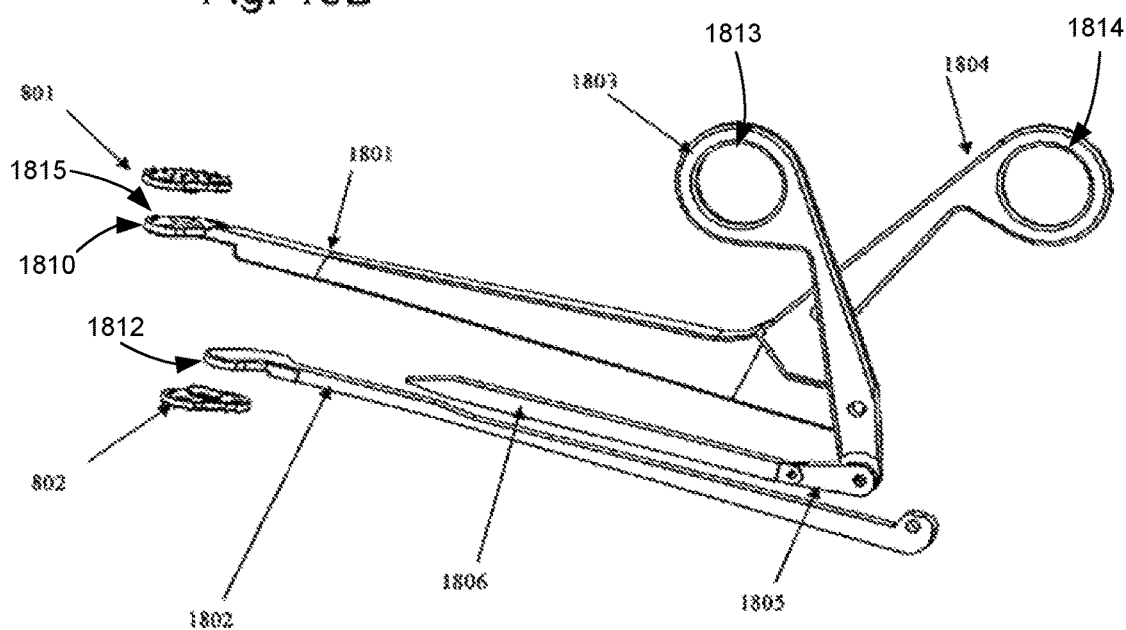
Figure 19A:
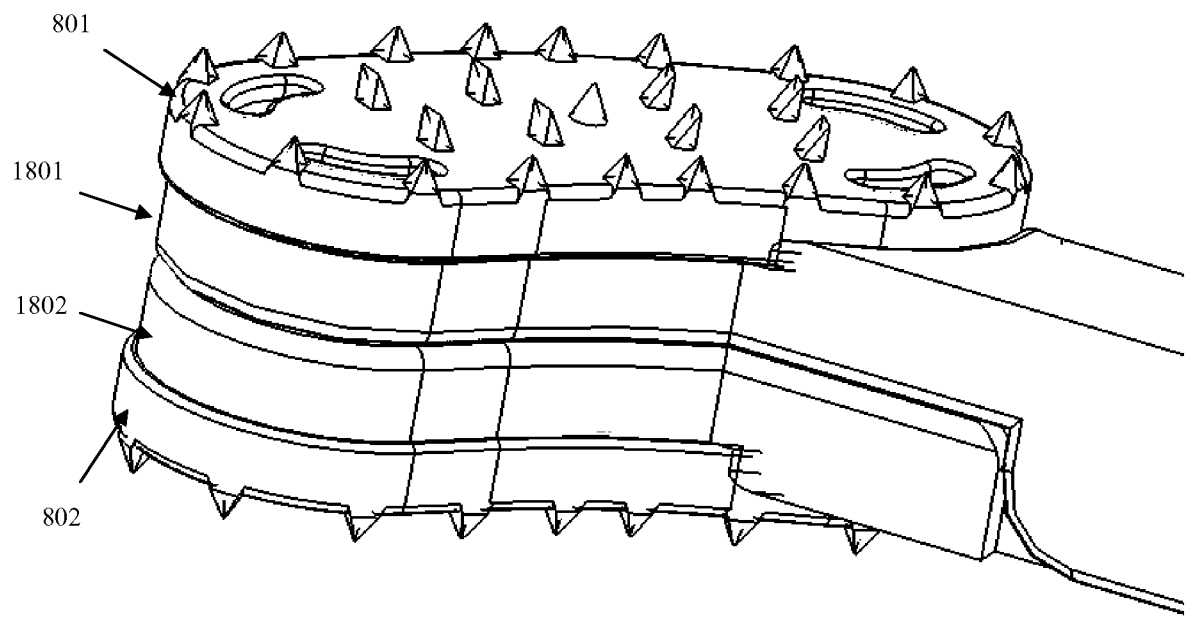
FIGS. 19A and 19B illustrate a detailed view of the plate insertion section of the external insertion device and the motion of the wedged separator expanding the disc plates.
Figure 19B:
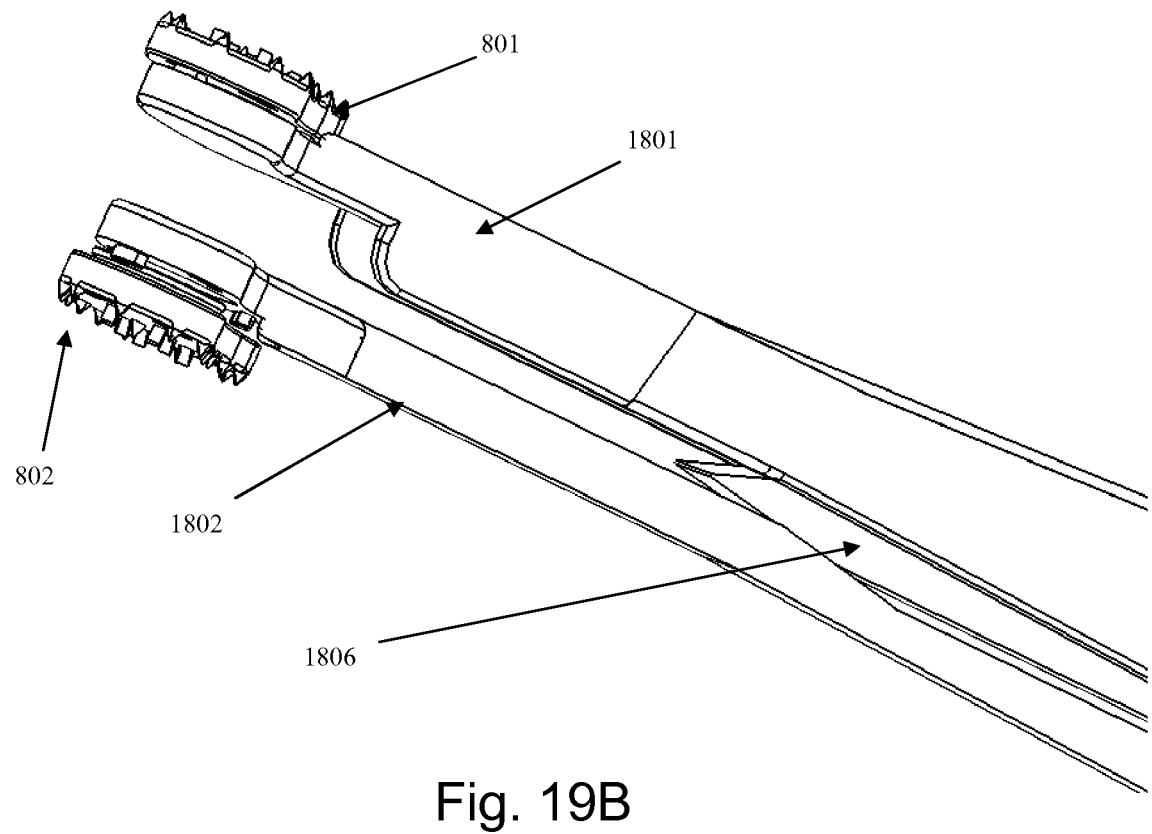

FIGS. 18A, 18B, 18C, 19A and 19B illustrate the insertion device 1800. The superior separator 1801 and inferior separator 1802 (FIGS. 18C and 19A and B) have extensions which are shaped exactly like the artificial disc plates 801, 802 and their cradles 1810, 1812 include alignment features 1815 that fit into the alignment slots 805 of the plates 801, 802 (FIGS. 10A and B and 19A and B). The lateral manipulator 1804 and medial manipulator 1803 (FIGS. 18A-19A and B) when opened lead to superior plate 801 and inferior plate 802 separation, and cause substantially parallel alignment of superior and inferior plate 801, 802 penetration into opposing vertebral bodies. The medial and lateral manipulators 1803, 1804 are attached by a transmission linkage 1805 (FIG. 18C). The action wedge 1806 upon manual opening of the instrument 1800 by the surgeon inserting his fingers into the manipulator digit insert 1807 (FIG. 18A) forces the wedge 1806 down in between the superior and inferior separators 1801, 1802 leading to superior disc plate 801 and inferior disc plate 802 separation, expansion and penetration into the superior and inferior vertebral bodies. The medial and lateral manipulators 1803, 1804 include digit inserts 1813, 1814 for the operator of the tool.

The Surgical Method of FIGS. 8-19

The surgical steps necessary to practice the present invention will now be described.

After the adequate induction of anesthesia the patient is positioned prone on a fluoroscopically amenable table. A unilateral hemi-laminotomy is performed. The procedure can be performed microscopically, endoscopically or tubularly in routine manner. A routine discectomy is performed. The superior and inferior disc plates alignment slots 805 are inserted into the cradles of the insertion device 1800. The nerve root is gently retracted and the disc plates 801, 802 are inserted into the disc space attached to the inserting/spreading device 1800. Under fluoroscopic guidance the plates 801, 802 are then placed at the center of gravity of the vertebral plates i.e. at the anterior-posterior and dorsal-ventral centers. When confirmed radiographically, the surgeon spreads the spreader 1800 which drives the wedge 1806 between the separators 1801, 1802 (FIG. 10) until the plates 801, 802 have penetrated and incorporated into the superior and inferior vertebral bodies. The inserter/spreader 1500 is then removed. The opposing plates 801, 802 are now substantially perfectly opposed to each other. The distance between the superior and inferior troughs 806 are now measured, and the surgeon selects from a selection of balls 803 of different heights to fit between the plates 801, 802, depending on patient size, etc. Using a forceps or similar instrument the ball 803 with the ball limiters 804 (embodiment I), or the ball with raised edges (embodiment II) are inserted in-between the superior and inferior troughs 806. During insertion of the ball 803 the superior and inferior leaflets 1202, 1201 of the limiters 804 are aligned with each other. After the ball 803 is inserted, the superior and inferior leaflets 1202, 1201 using a forceps are separated to effectively prevent ball extrusion and prevent completely unrestrained motion. After inserting the ball of embodiment II of FIGS. 15A-17B, the correct sized ball is simply inserted in between the two plates. The wound is then closed routinely.

The current device can easily be adapted for placement in cervical and thoracic discs. It may also be suitable for multiple level placements. This current device enables the restoration of motion of diseased discs with minimal anatomical destruction and invasiveness, and avoids the serious complications of anteriorly placed discs. Furthermore when an anteriorly placed lumbar disc is removed, it is extremely technically challenging. Furthermore the artificial disc is then replaced by a fusion device limiting motion. The posterior unilateral placement of this device obviates all the above mentioned risks. The device presented here is safely implanted avoiding anterior vascular structures and nerves which control ejaculation. It is also easily and safely explanted if necessary. The ease and safety of the insertion of this device heralds in a new era of safe and simple artificial lumbar disc technology.

What is claimed is:

1. An artificial disc system comprising:
   an artificial disc comprising:
   a first plate configured to occupy a space defined by a first vertebral endplate of a spine, the first plate including a first endplate-engaging surface having a first plurality of anchors, a first core-engaging surface positioned opposite the first endplate-engaging surface, and a first perimeter surface extending around a first perimeter of the first plate between the first endplate-engaging surface and the first core-engaging surface, wherein the first core-engaging surface comprises a concave core-engaging portion, wherein the first plurality of anchors comprise a first group of at least four anchors extending from the first endplate-engaging surface on a left side of the first endplate-engaging surface and a second group of at least four anchors extending from the first endplate-engaging surface on a right side of the first endplate-engaging surface, wherein each anchor in the first and second groups of the at least four anchors is positioned on the first endplate-engaging surface adjacent the first perimeter surface of the first plate such that each anchor in the first and second groups of the at least four anchors has an exterior surface that extends continuously from the first perimeter surface;
   a second plate configured to occupy a space defined by a second vertebral endplate of the spine, the second plate including a second endplate-engaging surface having a second plurality of anchors, a second core-engaging surface positioned opposite the second endplate-engaging surface, and a second perimeter surface extending around a second perimeter of the second plate between the second endplate-engaging surface and the second core-engaging surface, wherein the second plurality of anchors comprise a third group of at least four anchors extending from the second endplate-engaging surface on a left side of the second endplate-engaging surface and a fourth group of at least four anchors extending from the second endplate-engaging surface on a right side of the second endplate-engaging surface, wherein each anchor in the third and fourth groups of the at least four anchors is positioned on the second endplate-engaging surface spaced inward of the second perimeter surface of the second plate such that each anchor in the third and fourth groups of the at least four anchors is entirely offset from the second perimeter surface; and
   a mobile core sized and configured to be positioned between the first and second plates to space the first plate from the second plate and to permit the first and second plates to move relative to one another, wherein the mobile core has first and second plate-engaging surfaces that engage the first and second core-engaging surfaces of the first and second plates respectively, wherein the first and second plate-engaging surfaces of the mobile core are configured to slide against the first and second core-engaging surfaces of the first and second plates, respectively, wherein the first plate-engaging surface of the mobile core has a convex dome portion shaped to mate with the concave core-engaging portion of the first core-engaging surface of the first plate, wherein the mobile core is engaged with the first and second plates such that the first plate can move with respect to the second plate to accommodate lateral bending, flexion, extension, and rotation, and wherein a plurality of raised barriers or protrusions are positioned with respect to the mobile core to partially limit motion of the mobile core with respect to the first and second plates, wherein the raised barriers or protrusions are positioned inward of the second perimeter surface so as to define a gap between the second perimeter surface and the raised barriers or protrusions on the left and right sides of the second plate.

2. The artificial disc system of claim 1, wherein the mobile core comprises polyethylene and at least one of the first and second plates comprises cobalt chromium.

3. The artificial disc system of claim 1, wherein the mobile core comprises polyethylene and at least one of the first and second plates comprises titanium.

4. The artificial disc system of claim 1, wherein the convex dome portion of the first plate-engaging surface of the mobile core has a first height and a first radius with the first height being less than the first radius.

5. The artificial disc system of claim 1, wherein the mobile core has a first width along an x-axis from a core front to a core back and a second width along a y-axis from a first core side to a second core side, and wherein the second width is equal to the first width.

6. The artificial disc system of claim 1, wherein the first and second plates are configured to move with respect to the mobile core such that the first and second plates can have a substantially parallel relative orientation as well as a plurality of nonparallel relative orientations.

7. The artificial disc system of claim 1, wherein the artificial disc is sized and configured to be a cervical artificial disc to be inserted in a cervical disc space.

8. The artificial disc system of claim 1, wherein the mobile core comprises one or more projections configured to engage the raised barriers or protrusions.

9. The artificial disc system of claim 1, wherein:
   the first plurality of anchors also comprises a fifth group of anchors, in addition to the first group of the at least four anchors and the second group of the at least four anchors, positioned at locations spaced inward of the first perimeter surface, such that each anchor in the fifth group of the at least four anchors is entirely offset from the first perimeter surface; and
   the second plurality of anchors also comprises a sixth group of anchors, in addition to the third group of the at least four anchors and the fourth group of the at least four anchors, positioned adjacent the second perimeter surface, such that each anchor in the sixth group of the at least four anchors has an exterior surface that extends continuously from the second perimeter surface.

10. The artificial disc system of claim 1, and further comprising:
a surgical tool for inserting the artificial disc between the first and second vertebral endplates, the surgical tool comprising:
a handle portion;
an elongate insertion portion extending distally away from the handle portion; and
an implant holder connected at a distal end of the elongate insertion portion and having first and second portions sized and configured to engage the first and second plates so as to hold the first and second plates relatively firmly during insertion and positioning of the first and second plates between the first and second vertebral endplates in a disc space.

11. The artificial disc system of claim 10, wherein the first portion of the implant holder is hingedly connected to the second portion of the implant holder such that the first portion of the implant holder can be pivotably actuated with respect to the second portion of the implant holder via the handle portion.

12. The artificial disc system of claim 10, wherein the surgical tool attaches to the first and second plates without engaging the mobile core.

13. The artificial disc system of claim 1, wherein each of the first and second plates comprise means for engaging with an implant holder of a surgical tool.

14. The artificial disc system of claim 1, wherein the exterior surface of each anchor in the first and second groups of the at least four anchors extends continuously from the first perimeter surface such that the exterior surface of the respective anchor and a portion of the first perimeter surface together form an unbent, flat surface.

15. The artificial disc system of claim 1, wherein each anchor in the first and second groups of the at least four anchors is symmetric about a central dimension that runs through a center of the respective anchor.

16. The artificial disc system of claim 1, wherein each anchor in the third and fourth groups of the at least four anchors has a saw-tooth shape with triangular-shaped lateral sides and a horizontal top ridge that is parallel to the second endplate-engaging surface.

17. A method of operating the artificial disc system of claim 10, the method comprising:
gripping the first and second plates of the artificial disc via the implant holder of the surgical tool;
inserting the artificial disc into a patient along a surgical path via the surgical tool into a cervical disc space between the first and second vertebral endplates of the spine;
engaging the first and second vertebral endplates with the first and second plates of the artificial disc, such that the first and second plurality of anchors extend into the first and second vertebral endplates; and
releasing the first and second plates of the artificial disc and removing the surgical tool.

18. The method of claim 17, wherein the first portion of the implant holder is hingedly connected to the second portion of the implant holder such that the first portion of the implant holder can be pivotably actuated with respect to the second portion of the implant holder via the handle.

19. The method of claim 17, wherein the mobile core has a first width along an x-axis from a core front to a core back and a second width along a y-axis from a first core side to a second core side, and wherein the second width is equal to the first width.

20. The method of claim 17, wherein the artificial disc comprises a first artificial disc and wherein the cervical disc space comprises a first cervical disc space, the method further comprising performing multiple level placements, including the first artificial disc being inserted into the first cervical disc space and including a second artificial disc that is substantially similar to the first artificial disc being inserted into a second cervical disc space.

21. The method of claim 17, wherein each of the first and second plates comprise means for engaging with the implant holder of the surgical tool.

22. A method of operating an artificial disc system, the artificial disc system comprising:
an artificial disc comprising:
a first plate configured to occupy a space defined by a first vertebral endplate of a spine, the first plate including a first endplate-engaging surface having a first plurality of anchors, a first core-engaging surface positioned opposite the first endplate-engaging surface, and a first perimeter surface extending around a first perimeter of the first plate between the first endplate-engaging surface and the first core-engaging surface, wherein the first core-engaging surface comprises a concave core-engaging portion, wherein the first plurality of anchors comprise a first group of at least four anchors extending from the first endplate-engaging surface on a left side of the first endplate-engaging surface and a second group of at least four anchors extending from the first endplate-engaging surface on a right side of the first endplate-engaging surface, wherein each anchor in the first and second groups of the at least four anchors are positioned on the first endplate-engaging surface adjacent the first perimeter surface of the first plate;
a second plate configured to occupy a space defined by a second vertebral endplate of the spine, the second plate including a second endplate-engaging surface having a second plurality of anchors, a second core-engaging surface positioned opposite the second endplate-engaging surface, and a second perimeter surface extending around a second perimeter of the second plate between the second endplate-engaging surface and the second core-engaging surface, wherein the second plurality of anchors comprise a third group of at least four anchors extending from the second endplate-engaging surface on a left side of the second endplate-engaging surface and a fourth group of at least four anchors extending from the second endplate-engaging surface on a right side of the second endplate-engaging surface, wherein each anchor in the third and fourth groups of the at least four anchors are positioned on the second endplate-engaging surface spaced inward of the second perimeter surface of the second plate such that each anchor in the third and fourth groups of the at least four anchors is entirely offset from the second perimeter surface;
a mobile core sized and configured to be positioned between the first and second plates to space the first plate from the second plate and to permit the first and second plates to move relative to one another, wherein the mobile core has first and second plate-engaging surfaces that engage the first and second core-engaging surfaces of the first and second plates respectively, wherein the first and second plate-engaging surfaces of the first and mobile core are configured to slide against the first and second core-engaging surfaces of the first and second plates, respectively, wherein the first plate-engaging surface of the mobile core has a convex dome portion shaped to mate with the concave core-engaging portion of the first core-engaging surface of the first plate, wherein the mobile core is engaged with the first and second plates such that the first plate can move with respect to the second plate to accommodate lateral bending, flexion, extension, and rotation, and wherein a plurality of raised barriers or protrusions are positioned with respect to the mobile core to partially limit motion of the mobile core with respect to the first and second plates, wherein the raised barriers or protrusions are positioned inward of the second perimeter surface so as to define a gap between the second perimeter surface and the raised barriers or protrusions on the left and right sides of the second plate; and a surgical tool for inserting the artificial disc between the first and second vertebral endplates, the surgical tool comprising:
  a handle portion;
  an elongate insertion portion extending distally away from the handle portion; and
  an implant holder connected at a distal end of the elongate insertion portion and having first and second portions sized and configured to engage the first and second plates so as to hold the first and second plates relatively firmly during insertion and positioning of the first and second plates between the first and second vertebral endplates in a disc space;

the method comprising:
  gripping the first and second plates of the artificial disc via the implant holder of the surgical tool;
  inserting the artificial disc into a patient along a surgical path via the surgical tool into a cervical disc space between the first and second vertebral endplates of the spine, wherein the mobile core is placed between the first and second plates after the first and second plates are inserted into the cervical disc space;
  engaging the first and second vertebral endplates with the first and second plates of the artificial disc, such that the first and second plurality of anchors extend into the first and second vertebral endplates; and
  releasing the first and second endplates of the artificial disc and removing the surgical tool.

* * * * *